(12) United States Patent
Liu et al.

(10) Patent No.: US 8,507,290 B2
(45) Date of Patent: Aug. 13, 2013

(54) WATER-SOLUBLE SILSESQUIOXANES AS ORGANIC QUANTUM DOTS FOR SENSING AND IMAGING

(75) Inventors: Bin Liu, Singapore (SG); Kanyi Pu, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/498,985

(22) PCT Filed: Sep. 28, 2010

(86) PCT No.: PCT/SG2010/000366
§ 371 (c)(1),
(2), (4) Date: Mar. 29, 2012

(87) PCT Pub. No.: WO2011/040882
PCT Pub. Date: Apr. 7, 2011

(65) Prior Publication Data
US 2012/0190125 A1 Jul. 26, 2012

Related U.S. Application Data

(60) Provisional application No. 61/246,623, filed on Sep. 29, 2009.

(51) Int. Cl.
*G01N 21/64* (2006.01)
*G01N 33/50* (2006.01)
*C07F 7/21* (2006.01)

(52) U.S. Cl.
USPC ............. 436/172; 436/63; 556/461; 548/110

(58) Field of Classification Search
None
See application file for complete search history.

(56) References Cited

U.S. PATENT DOCUMENTS

| 6,927,301 B2 * | 8/2005 | Laine et al. ............ 556/450 |
| 2006/0194068 A1 | 8/2006 | Kato et al. |
| 2007/0045619 A1 | 3/2007 | Park et al. |
| 2008/0029739 A1 * | 2/2008 | Jeganathan et al. ...... 252/301.35 |
| 2008/0171846 A1 * | 7/2008 | Ootake et al. ............ 528/25 |
| 2009/0203931 A1 * | 8/2009 | Ohrlein et al. ............ 556/418 |
| 2010/0038526 A1 * | 2/2010 | Loy et al. .................. 250/226 |
| 2010/0280561 A1 * | 11/2010 | Song et al. ................ 606/86 R |

FOREIGN PATENT DOCUMENTS

WO 2007147742 12/2007

OTHER PUBLICATIONS

McCusker, C. et al. "Cationic polyhedral oligomeric silsesquioxane (POSS) units as carriers for drug delivery processes," Chem. Commun., 2005, 996-998.*

Gnanasekaran, D.J., et al., Developments of Polyhedral Oligomeric Silsesquioxanes (POSS), POSS Nanocomposites and their Applications: A Review, Scientific and Industrial Research, 2009, vol. 68, pp. 437-464.

Abad, M. J. et al., Epoxy Networks Containing Large Mass Fractions of a Monofunctional Polyhedral Oligomeric Silsesquioxane, Macromolecules, 2003, vol. 36, pp. 3128-3135.

International Search Report, Apr. 18, 2011, Counterpart International Patent Application No. PCT/SG2010/000366.

* cited by examiner

*Primary Examiner* — Yelena G Gakh
*Assistant Examiner* — Michelle Adams
(74) *Attorney, Agent, or Firm* — Lathrop & Gage LLP; Brian C. Trinque

(57) ABSTRACT

The present invention generally relates to water-soluble, highly fluorescent polyhedral oligomeric silsesquioxane (POSS) compounds useful for sensing and bioimaging applications.

20 Claims, 12 Drawing Sheets

R = -(CH₂)₆N(CH₃)₃Br
    ⊕         ⊖

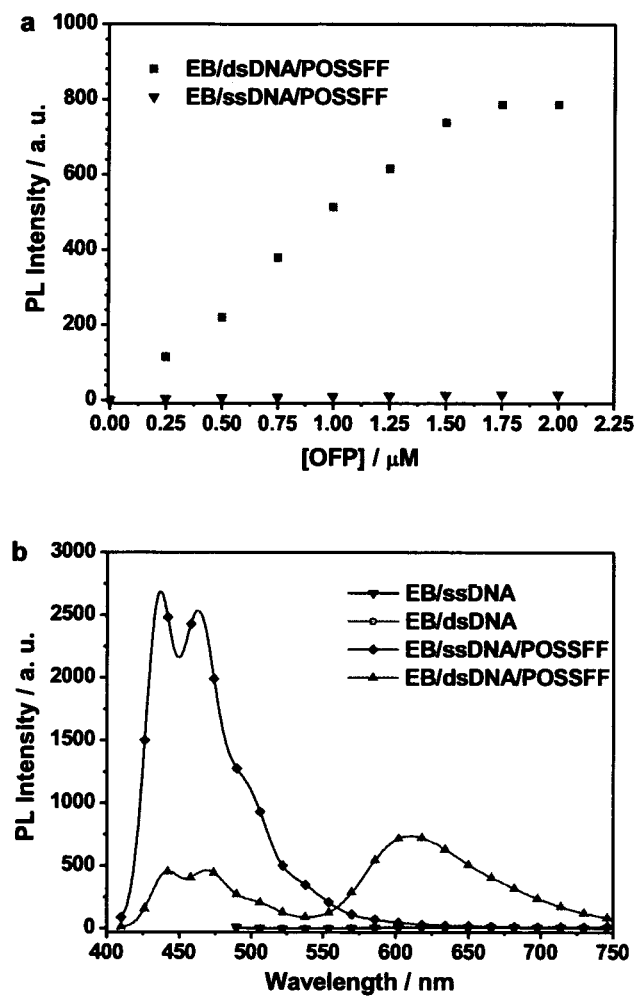
FIG. 6A-B

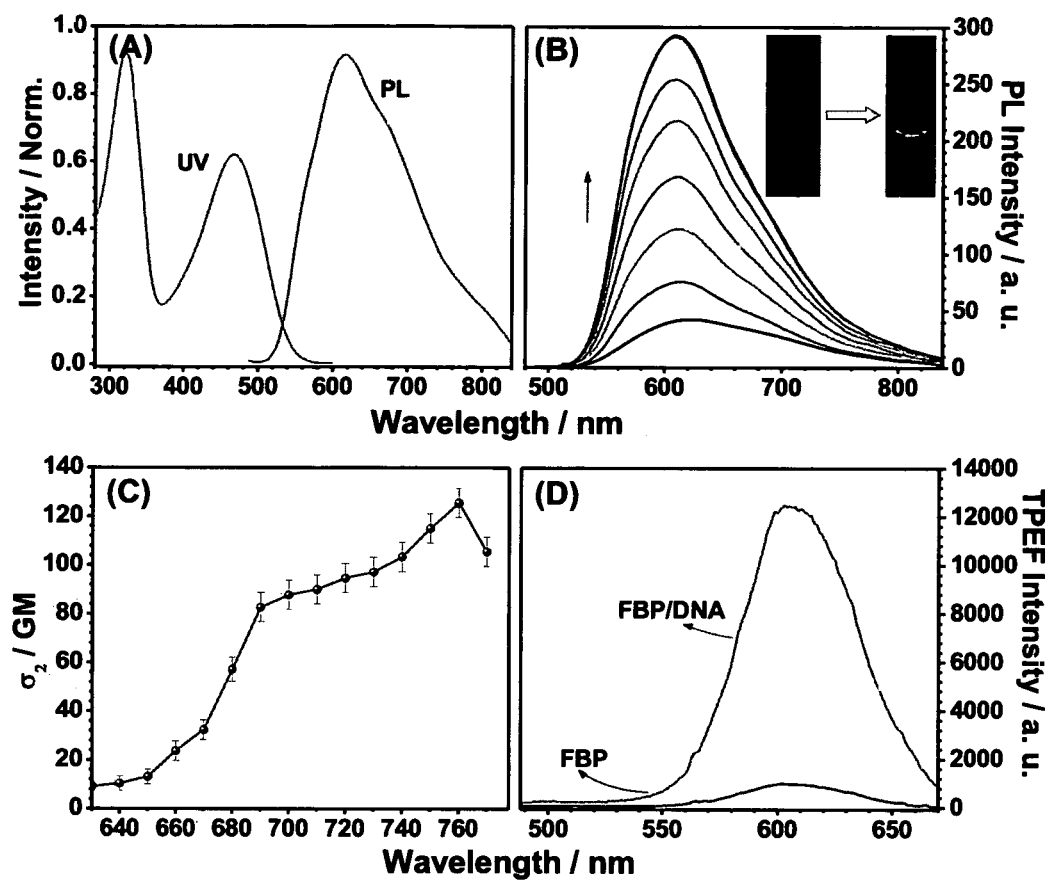
FIG. 7A-D

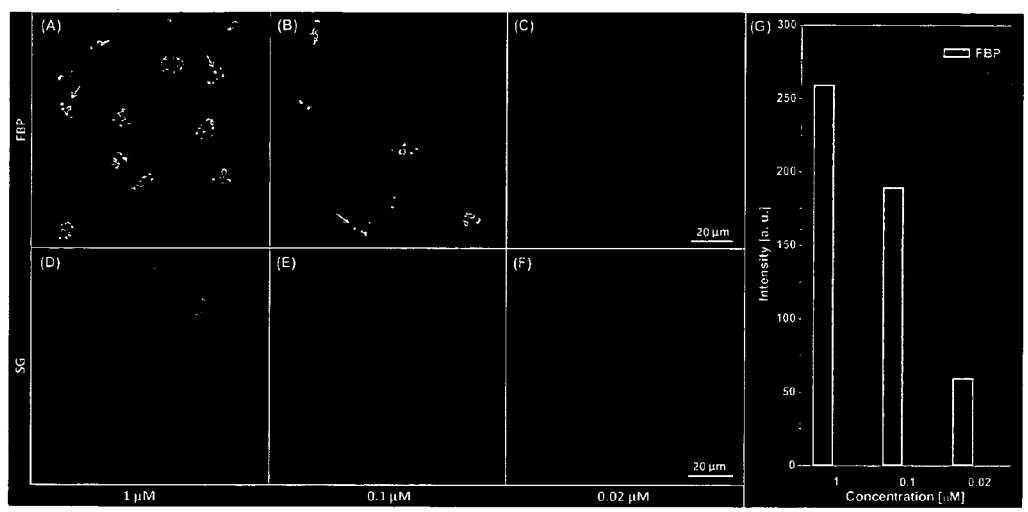
FIG. 10A-G

WATER-SOLUBLE SILSESQUIOXANES AS ORGANIC QUANTUM DOTS FOR SENSING AND IMAGING

RELATED APPLICATIONS

This application is a 35 U.S.C. §371 filing of International Patent Application No: PCT/SG2010/000366, which was filed on Sep. 28, 2010, and which claims priority to U.S. Provisional Application No: 61/246,623, which was filed on Sep. 29, 2009. The entire contents of the aforementioned applications are hereby incorporated herein by reference.

BACKGROUND OF THE INVENTION

The nucleus within a eukaryotic cell is a complex but well-organized dynamic architecture that accommodates gene expression, replication, recombination and repair, as well as RNA processing and ribosome subunit assembly, making it the central hub for the determination of cell fate. Since variations in nuclear structures provide important diagnostic and prognostic information for pathologists, nucleus imaging is of vital concernment in the field of bioimaging.

Fluorescent materials have been proven to be a powerful implement for biological applications, including biosensors and cellular imaging. Since small fluorophores suffer from low photobleaching thresholds that limit their effectiveness in long-term and multi-dimensional applications, semiconductor quantum-dots (QDs) have emerged as a category of bright and photostable alternatives. However, QDs tend to aggregate and lose their luminescence in acid environments, (pH<5) or isotonic conditions. Moreover, the intrinsically-toxic elements within QDs, such as cadmium and selenium, are liable to release and in turn render toxicity, especially in radiation-caused oxidation environment. Although surface modification of QDs with biomolecules or biocompatible polymers could mitigate these detrimental problems, this strategy is complicated, and time-consuming. More importantly, surface modification often has a negative impact on the luminescence and dimension of QDs. As such, new fluorescent nanomaterials with high photoluminescence (PL) quantum yield, good photostability and biocompatibility remain in urge demand for optical biological applications.

SUMMARY OF THE INVENTION

The invention generally relates to water-soluble, highly fluorescent polyhedral oligomeric silsesquioxane (POSS) compounds for sensing and bioimaging applications. The general chemical structure of these compounds is as follows:

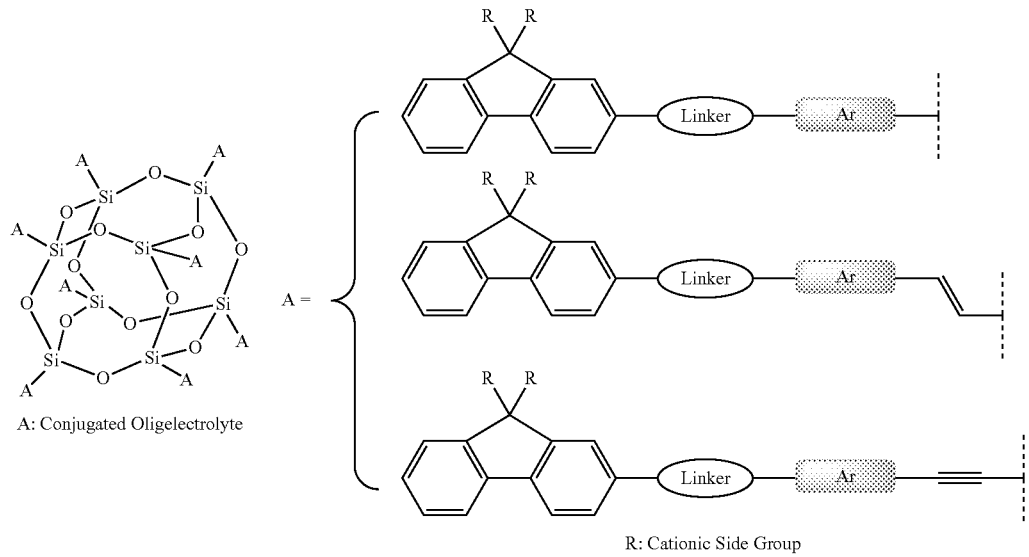

A: Conjugated Oligelectrolyte

R: Cationic Side Group

The POSS compound is assembled by substituting the silicon atoms of the POSS core with a conjugated polyelectrolyte (CPE) or a conjugated oligoelectrolyte (COE), as represented by A. CPEs and COEs are water-soluble fluorene based dimers, and are attached to a silicon atom of POSS through a single bond, double bond and triple bond. The structure of a CPE or a COE includes Ar, which may be any aromatic group. For example, Ar can be selected from fluorene, benzene, biphenyl, pyridine, bipyridinium, triphenylamine, anthracene, thiophene, carbazole, or benzothiadiazole. The fluorene of the COE or CPE may be substituted with R. Each R may be independently selected from hydrogen, a cationic alkyl side group (for example, —$(CH_2)_n NMe_3 X$ or —$(CH_2)_n NMe_3 X$, where n=3-13), and cationic oligo(ethylene oxide) group (for example, —$(CH_2CH_2O)_n NMe_3 X$ or —$(CH_2CH_2O)_n NMe_3 X$, where n=3-13). Each R may be independently selected from hydrogen, a cationic alkyl side group (for example, —$(CH_2)_n NMe_3 X$, where n=3-13), and cationic oligo(ethylene oxide) group (for example, —$(CH_2CH_2O)_n NMe_3 X$ where n=2-100). The anionic counterion X is selected from, but is not limited to, for example, $Br^-$, $I^-$, $BF_4^-$, $CF_3SO_3^-$, ammonium hexafluorophosphate, and tetrakis[3,5-bis(trifluoromethyl)phenyl]borate.

Another general class of chemical structure is a compound represented by the following structural formula:

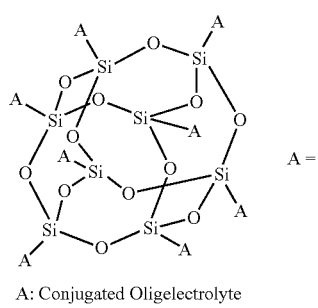

A: Conjugated Oligelectrolyte

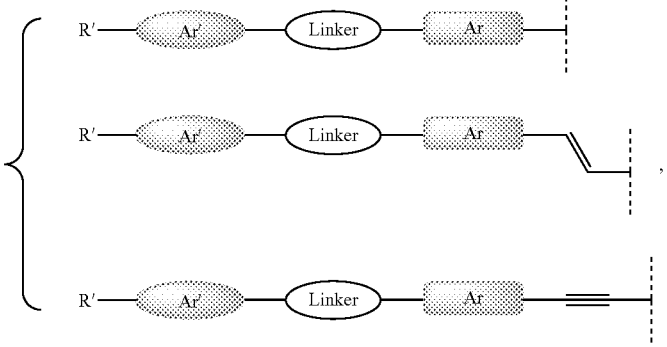

or an acceptable salt thereof; wherein
Each

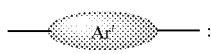

is independently selected from:

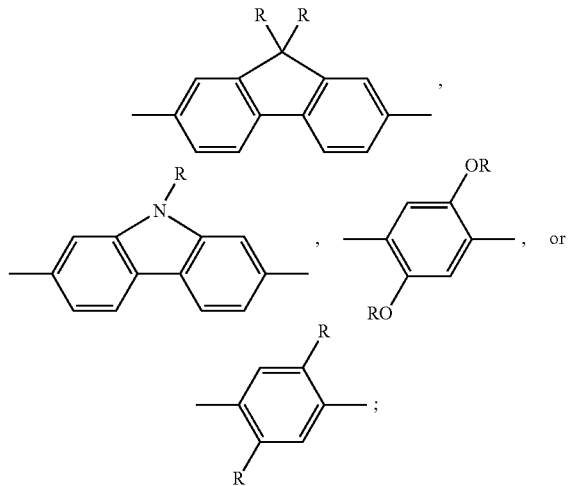

Each Ar is independently an optionally substituted aromatic group;

Each R is independently a cationic, anionic, or neutral alkyl group or a cationic, anionic, or neutral oligo(ethylene oxide) group;

Each Linker is a single bond, double bond, triple bond, —CH$_2$— or —CH$_2$CH$_2$—;

Each R' is independently H or a terminal reactive group.

The POSS compounds of the invention are organic-inorganic hybrid nanomaterials that possess high photoluminescence quantum yields in biological media and excellent environmental stability and photostability, which can be used in biosensor and bioimaging.

BRIEF DESCRIPTION OF THE DRAWINGS

The foregoing will be apparent from the following more particular description of example embodiments of the invention, as illustrated in the accompanying figures.

FIG. 6A is a graph showing the PL intensity of EB at 610 nm as a function of [POSSFF] for EB/ssDNA and EB/dsDNA mixtures upon excitation at 390 nm.

FIG. 6B is a graph showing the PL spectra of EB, EB/ssDNA and EB/dsDNA in the absence and presence of 1.4 µg mL$^{-1}$ POSSFF.

FIG. 7A is the normalized UV-Vis and PL spectra of POSSFBT in water. Excitation at 460 nm.

FIG. 7B is the PL spectra of 2 µM POSSFBT in 25 mM PBS (pH=7.4) in the absence and presence of DNA with [DNA] ranging from 0 to 3.2 µM at the intervals of 0.4 upon excitation at 460 nm. Inset shows the photographs of the fluorescence solutions of POSSFBT in the absence (left) and presence (right) of 3.2 µM DNA under UV radiation at 365 nm.

FIG. 7C is the two-photon absorption (TPA), spectrum of 2 µM POSSFBT in water. 1 GM=1×10$^{-50}$·cm$^4$·s·photon$^{-1}$·molecule$^{-1}$.

FIG. 7D is the two-photon excited fluorescence (TPEF) spectra of 2 µM POSSFBT (labelled as FBP in the figure) in the absence and presence of 3.2 µM DNA upon excitation at 760 nm.

FIG. 10A-F are one-photon excited fluorescence (OPEF) images of MCF-7 cells incubated with different concentration of FBP (A-C) or SYBR Green I (SG) (D-F) for 2 h. [FBP] is 1, 0.1 and 0.02 µM for images A, B and C, respectively. [SG] is 1, 0.1 and 0.02 µM for images D, E and F, respectively. The fluorescence signals are collected above 560 nm excited at 488 nm. These experiments were conducted under the same confocal laser scanning microscopy (CLSM) settings. Images A-C share the same scale bar, the same for images D-F.

FIG. 10G is a graph depicting fluorescence intensities of the cellular nuclei as a function of dye concentration. The data are extracted from images FIG. 9A-F.

DETAILED DESCRIPTION OF THE INVENTION

Figure 1:
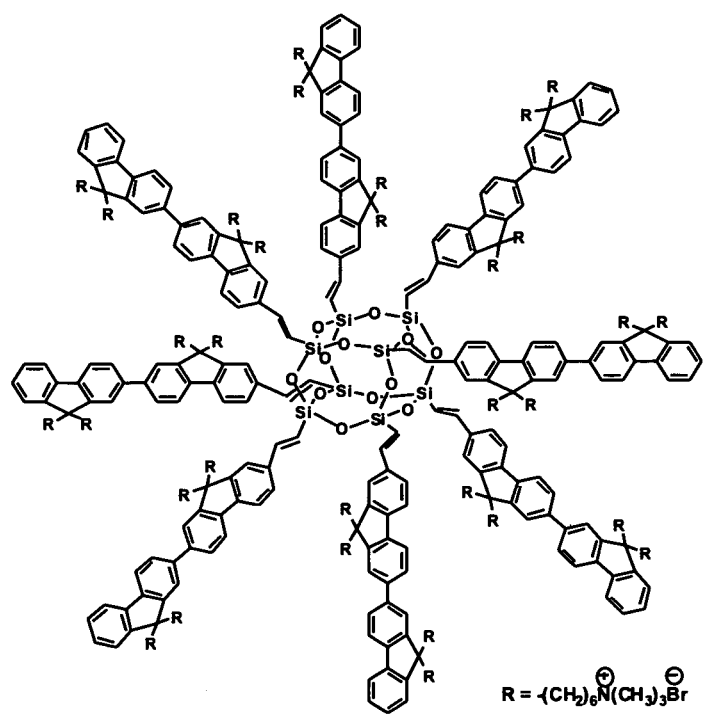
FIG. 1 is the chemical structure of POSSFF.

A description of example embodiments of the invention follows.

The teachings of all patents, published applications and references cited herein are incorporated by reference in their entirety.

Fluorescent nanomaterials have been widely applied in sensory and biological applications. Although semiconductor quantum-dots (QDs) have emerged as a category of alternatives for organic dyes, the concentration dependent cytotoxicity of QDs, mainly caused by oxidative degradation of the heavy metal components, remains a problem although various modifications have been made to coat QD cores with ZnS shell or further encapsulate QDs with biocompatible polymeric matrixes. Stabilization of QDs in biological systems requires severe surface modification, eventually imparting thick shells that preclude them from entering nucleus.

Both long-term and multi-dimensional imaging and sensitive biosensors require the fluorescent materials to have excellent photostability and to produce sharp brightness. In comparison with small molecules that tend to be barred to the cytoplasm during cellular uptake, nanoparticles are more likely to traverse the nuclear pore complex (NPC) to the nucleus by passive diffusion. By virtue of its advantages over one-photon fluorescence, including reduced photodamage, improved spatiotemporal resolution, decreased Raman scattering, and minimized cellular autofluorescence, two-photon fluorescent nucleus imaging is highly desirable. Despite these advantages, two-photon fluorescent technologies are rarely exploited due to the lack of two-photon absorption (TPA) chromophores that can selectively stain the nucleus. Designing TPA nanomaterials for two-photon fluorescence imaging of nucleus remained a challenge at the time of our invention.

Water-soluble organic-inorganic hybrid nanomaterials which have the merits of inorganic dots, but with extremely low (or no) cytotoxicity are described herein. These nanomaterials are conjugated oligomer substituted polyhedral oligomeric silsesquioxanes (POSS), which have the high photoluminescence quantum yields in biological media, good environmental stability and long-term stability. These hybrid nanomaterials can be utilized as efficient light-harvesting molecules for optical amplifications in biosensor and bioimaging. Participation of these nanomolecules in biological assays can significantly enhance the fluorescent signal, ultimately allowing naked-eye detection of biomolecules in trace amount. The advantages of the compounds of the invention include a reduction in the amount of dye and laser power required to give bright and clear images.

Polyhedral oligomeric silsesquioxanes (POSS) are a category of polycyclic compounds, which consist of a silicon/oxygen cage surrounded by tunable organic substitution groups. Due to the nano-scaled dimension and facile modification of substitution groups, POSS serves as organic-inorganic nanobuilding blocks for construction of fluorescent nanomaterials. Although some fluorescent POSS have been reported, most of them are synthesized by attachment of organic dyes to POSS, which have low solubility and therefore, limited biological application.

Conjugated polyelectrolytes (CPEs) and conjugated oligoelectrolytes (COEs) are fluorescent macromolecules with electron-delocalized backbone and water-soluble side chains. There functional materials combine the light-harvesting properties of conjugated polymers with electrostatic behaviors of electrolytes, providing unique opportunities for construction of sensory and imaging materials. The hydrophobic aromatic backbones of COEs can result in polymer aggregation and often result in self-quenching of the fluorescence in aqueous media, an effect worsened at elevated ionic strength. The CPEs and COEs used herein, when attached to POSS, have minimized self-quenching behaviors, and are therefore desirable for optical applications.

Figure 2:
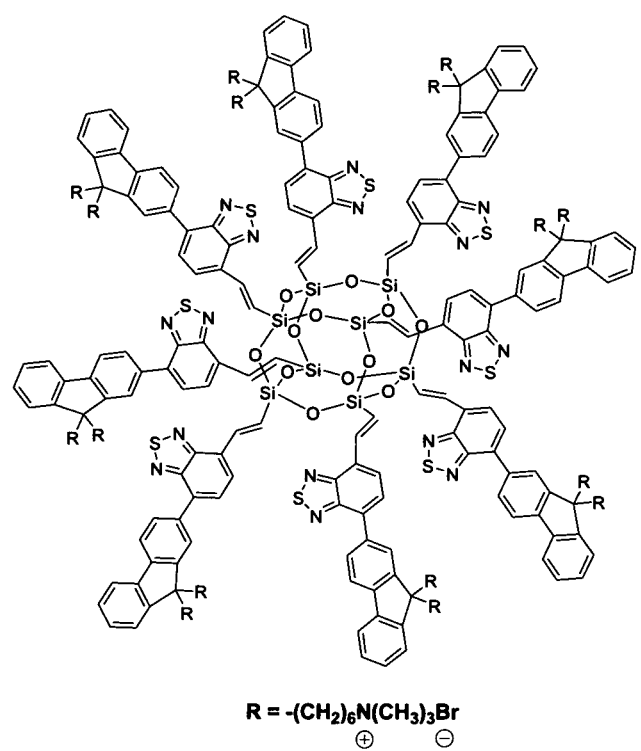
FIG. 2 is the chemical structure of POSSFBT.

A water-soluble hybrid unimolecular nanoparticle based on polyhedral oligomeric silsesquioxane (POSS) and conjugated oligoelectrolyte (COE) for two-photon fluorescent nucleus imaging is described herein. The three-dimensional macromolecule (POSSFF, FIG. 1 and POSSFBT, FIG. 2) is composed of a rigid silicon-oxygen cage surrounded by the cationic COE arms on its globular periphery. This unique nanostructure provides nucleus permeability and light-up response toward DNA, enabling to selectively illuminate the nucleus structure with a high contrast.

Figure 3:
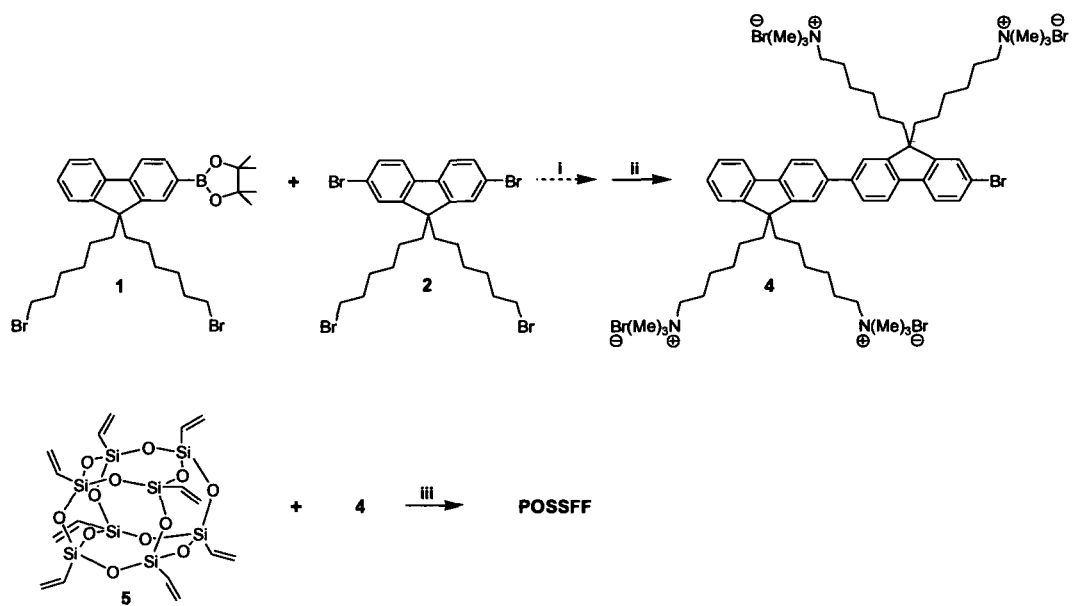
FIG. 3 is a synthetic scheme for POSSFF. Reagents and conditions: i) Pd(PPh$_3$)$_4$, Na$_2$CO$_3$, toluene/H$_2$O, 90° C., 48 h; ii) THF/H$_2$O, NMe$_3$, 24 h; iii) Pd(OAc)$_2$/P(o-tolyl)$_3$, DMF/TEA, 100° C., 36 h.
Figure 4:
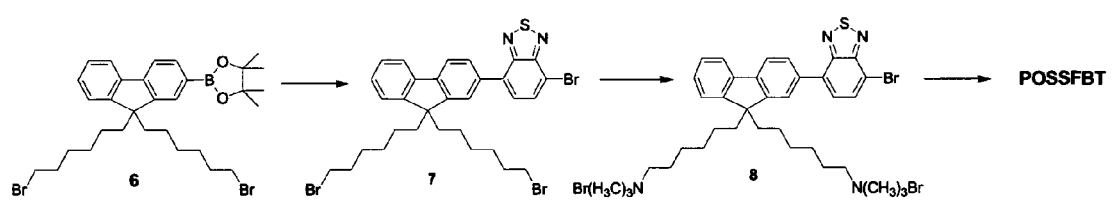
FIG. 4 is a synthetic scheme for POSSFBT.

Cationic oligofluorene substituted POSS compounds are nanomaterials that are efficient light-harvesting antennas for optical amplification in biosensor and cellular imaging. The synthetic route toward POSSFF is depicted in FIG. 3. The synthesis of POSSFBT is similar to the strategy described above for POSSFF and is depicted in FIG. 4.

In summary, the synthesis involves the palladium-mediated Suzuki cross-coupling reaction between 2-(9,9-bis(6-bromohexyl)fluoren-2-yl)-4,4,5,5-tetramethyl-1,3,2-dioxaborolane (1) and 2,7-dibromo-9,9-bis(6-bromohexyl)fluorene (2) led to 2-(7-bromo-9,9-bis(6-bromohexyl)fluorenyl)-9,9-bis(6-bromohexyl)fluorene (3). Quaternization of 3 with trimethylamine afforded 2-(7-bromo-bis(6-N,N,N-trimethyl ammonium)hexyl)fluorenyl)-bis(6-N,N,N-trimethylammonium)hexyl)fluorene (4) in 98% yield. Finally, the water-soluble dimer 4 was reacted with octavinyl POSS (5) via a $Pd(OAc)_2/P(o-tolyl)_3$ catalyzed Heck coupling reaction to afford the cationic macromolecule POSSFF. Example 1 provides further synthetic details for both POSSFF and POSSFBT.

One embodiment of the invention is a polyhedral oligomeric silsesquioxane compound, herein referred to as a "POSS compound." As used herein, POSS compound is a compound that includes POSS core and either COE or CPE, or a mixture thereof, wherein the COE or CPE, or both is attached to the POSS core at the silicon atoms of the POSS core.

One embodiment of the invention is a compound represented by the following structural formula:

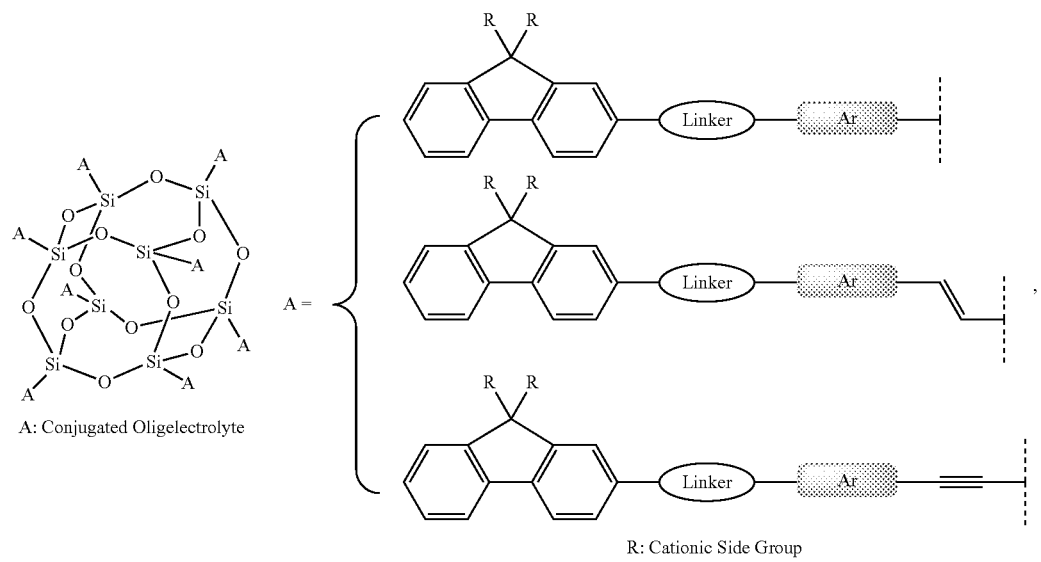

A: Conjugated Oligelectrolyte

R: Cationic Side Group or an acceptable salt thereof; wherein:

Ar is an optionally substituted aromatic group;

Linker is a single bond, double bond, triple bond, —CR$^1_m$—; wherein R$^1$ is hydrogen, halogen, hydroxy, amino, $C_1$-$C_6$alkyl, $C_1$-$C_6$alkenyl, $C_1$-$C_6$alkynyl, or $C_1$-$C_6$alkoxy; wherein the alkyl, alkenyl, alkynyl or alkoxy may be optionally substituted with halogen, hydroxy, $C_1$-$C_4$alkoxy or amino;

each R is independently hydrogen, a cationic alkyl side group or a cationic oligo(ethylene oxide) group. In a specific embodiment, m is 1 or 2.

One embodiment of the invention is a compound represented by the following structural formula:

or an acceptable salt thereof; wherein:

Ar is an optionally substituted aromatic group;

Each Linker is a single bond, double bond, triple bond, —CH$_2$— or —CH$_2$CH$_2$—;

and each R is independently hydrogen, a cationic alkyl side group or a cationic oligo(ethylene oxide) group.

In another embodiment of the invention is a compound represented by the following structural formula:

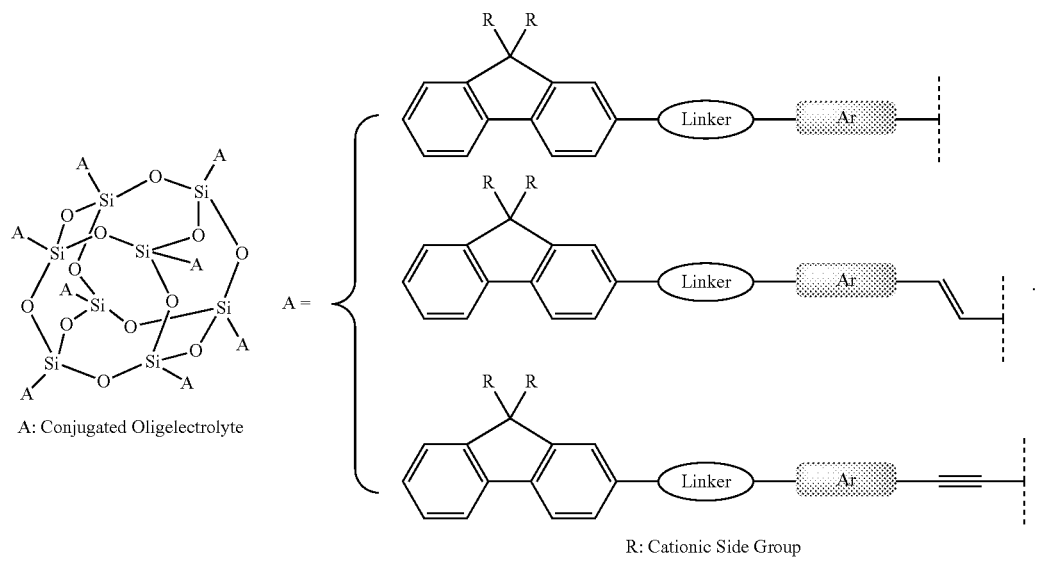

A: Conjugated Oligelectrolyte

R: Cationic Side Group

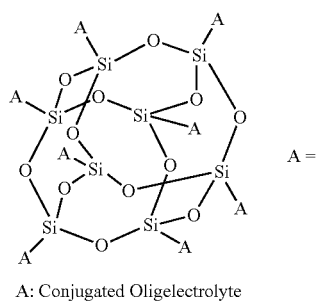

A: Conjugated Oligelectrolyte

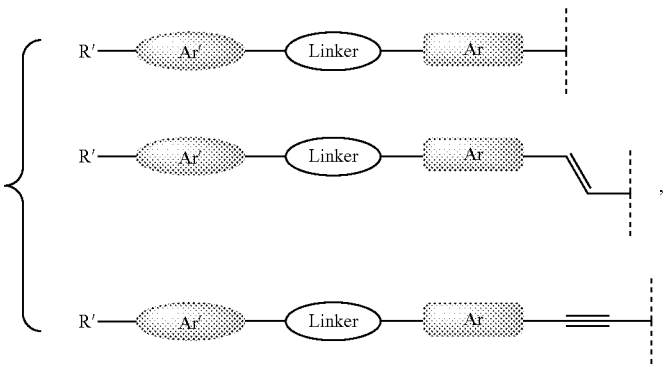

or
an acceptable salt thereof; wherein
Each

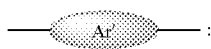

is independently selected from:

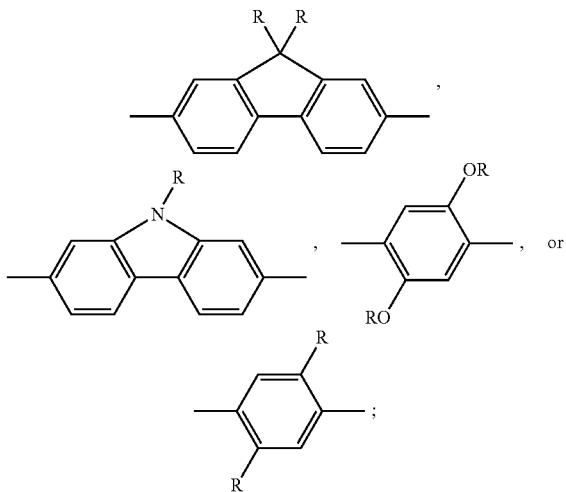

Each Ar is independently an optionally substituted aromatic group. Specifically, Ar can be independently selected from fluorene, benzene, biphenyl, pyridine, bipyridinium, triphenylamine, anthracene, thiophene, carbazole, or benzothiadiazole. Optional substituents include those defined by R.

Each R is independently a cationic, anionic, or neutral alkyl group or a cationic, anionic, or neutral oligo(ethylene oxide) group;

Each Linker is a single bond, double bond, triple bond, —CH$_2$— or —CH$_2$CH$_2$—;

Each R' is independently H or a terminal reactive group.

As used herein, "oligo" refers to a monomer unit repeating ten or less times in the chain. For example, "oligo(ethylene oxide) refers to an ethylene oxide repeat unit (e.g. (—CH$_2$CH$_2$O)$_n$, wherein n is 1-10; 2-10; 2-5; 5-10; 2-8; 2-6; or 3-6.

As used herein, "poly" refers to a monomer unit repeating ten or more times in the chain. For example, "poly(ethylene oxide) refers to an ethylene oxide repeat unit (e.g. (—CH$_2$CH$_2$O)$_n$, wherein n is greater than 10. Specifically, n is 10-100, 10-200; 10 to 50; or 50-100.

A cationic alkyl side group is an alkyl group that may be straight or branched and includes a moiety, such as an amine, that confers a positive charge. A cationic oligo(ethylene oxide) group is a polymer of ethylene oxide that includes a moiety, such as an amine, that confers a positive charge. The amine can be a primary, secondary, tertiary or a quaternary amine. Specifically, the amine is a quaternary amine. A cationic alkyl group includes, for example —(CH$_2$)$_n$NMe$_3$X where n=3-13; 3-5; 5-7; 7-9; 9-11; or 11-13; and specifically n is 6. A cationic oligo(ethylene oxide) group includes, for example, —(CH$_2$CH$_2$O)$_n$NMe$_3$X, where n=2-100; 2-50; 2-25; 2-15; 2-10; 2-5; 50-100; 25-50; 15-25; 10-15; or 5-10. The anionic counterion X is selected from, but is not limited to, for example, Br$^-$, I$^-$, BF$_4^-$, CF$_3$SO$_3^-$, ammonium hexafluorophosphate, and tetrakis[3,5-bis(trifluoromethyl)phenyl]borate.

A neutral alkyl side group is an alkyl group that may be straight or branched and is uncharged. An alkyl group may include 3-100 atoms. Specifically, an alkyl group may include 3-13 carbon atoms. Specifically, a neutral alkyl group is —(CH$_2$)$_n$CH$_3$; wherein n is 3-13; 5-13; 3-5; or 5-100. A neutral oligo(ethylene oxide) group is a polymer of ethylene oxide that is uncharged. A neutral group includes, but is not limited to oligo(ethylene oxide) and poly(ethylene oxide). Specifically, a neutral ethylene oxide group is —(CH$_2$CH$_2$O)$_n$CH$_3$; wherein n is 5-100; 5-50; 5-25; 5-15; 50-100; 25-50; 15-25; 10-15; or 5-10.

An anionic alkyl side group is an alkyl group that may be straight or branched and includes a moiety, such as an acid (sulfonic, phosphonic or carboxylic), that confers a negative charge. An anionic oligo(ethylene oxide) group or poly(ethylene oxide) group is a polymer of ethylene oxide that includes a moiety, such as an acid (sulfonic, phosphonic or carboxylic), that confers a negative charge. An anionic group includes: —(CH$_2$)$_n$X' or —(CH$_2$CH$_2$O)$_n$X'; wherein X' is selected from, but is not limited to, SO$_3^{2-}$Y$_2$, PO$_3^{2-}$Y$_2$, and CO$_2$Y and n is 3-100, 3-50; 3-25; 3-15; 3-10; 3-5; 50-100; 25-50; 15-25; 10-15; or 5-10. Alternatively, n is 2. Y is an alkali metal or an alkali earth metal. Specifically, Y is selected from, but is not limited to, Na$^+$ and K$^+$.

As used herein, a terminal reactive group includes, for example, COOH, NH$_2$, CHO, and SH. The presence of a terminal reactive group is to allow for bioconjugation of the POSS compound to antibodies. Conjugation to an antibody would allow for targeting capability of POSS compounds, ultimately making specific biosensing and bioimaging feasible.

Conjugation reactions are known to those of, skill in the art. For instance, when R' is —COOH or —NH$_2$, a carbodiimide-activated coupling reaction can be conducted between the POSS compounds and antibody molecule. The compound is first activated by 1-ethyl-3-(3-dimethylaminopropyl)carbodiimide (EDC) and N-hydroxysulfosuccinimide sodium salt (sulfo-NHS). Next, antibody is added. The product can be purified by dialysis or sodium dodecyl sulfate polyacrylamide gel electrophoresis. This representative coupling reaction yields the bioconjugate POSS-antibody compound with targeting capability. See Greg T. Hermanson, Ed. Bioconjugate techniques. Academic Press, 1996, the entire teachings of which are incorporated herein by reference, for description of coupling chemistry between NH$_2$ on a POSS core to —COOH or —CHO.

"Linker is a single bond" means, for example:

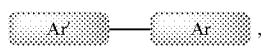

for example:

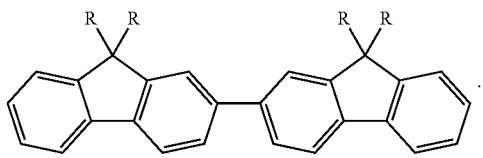

"Linker is a double bond" means, for example:

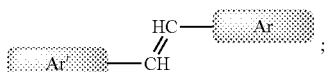

for example:

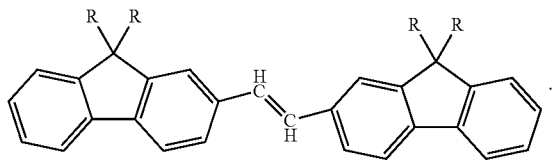

"Linker is a triple bond" means, for example:

for example

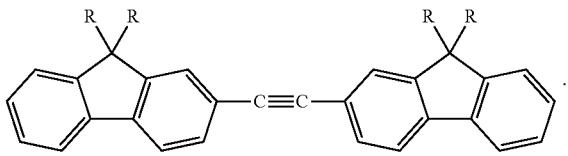

"Linker is —CH$_2$—" means, for example,

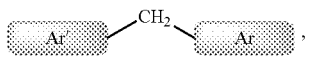

for example

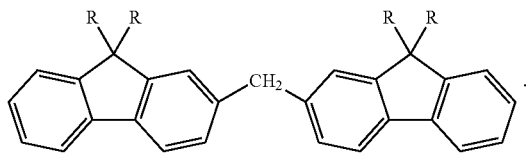

"Linker is —CH$_2$CH$_2$-" means, for example,

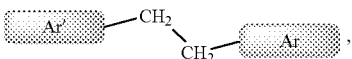

for example

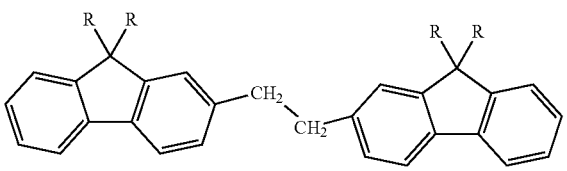

In a specific embodiment, Ar is selected from the group consisting of fluorene, benzene, biphenyl, pyridine, bipyridinium, triphenylamine, anthracene, thiophene, carbazole, and benzothiadiazole.

In another specific embodiment, each R is independently selected from the group consisting of hydrogen, —(CH$_2$)$_n$NMe$_3$X; —(CH$_2$)$_n$NMe$_3$X; —(CH$_2$O)$_n$NMe$_3$X; and —(CH$_2$O)$_n$NMe$_3$X); wherein X is an anionic counterion and n is 3 to 13. In another specific embodiment, each R is independently selected from the group consisting of hydrogen, —(CH$_2$)$_n$NMe$_3$X and —(CH$_2$O)$_n$NMe$_3$X); wherein X is an anionic counterion and n is 3 to 100.

In yet another specific embodiment, X is selected from Br$^-$, I$^-$, BF$_4^-$, CF$_3$SO$_3^-$, ammonium hexafluorophosphate, and tetrakis[3,5-bis(trifluoromethyl)phenyl]borate.

In a specific embodiment, the compound is represented by the following structural formula:
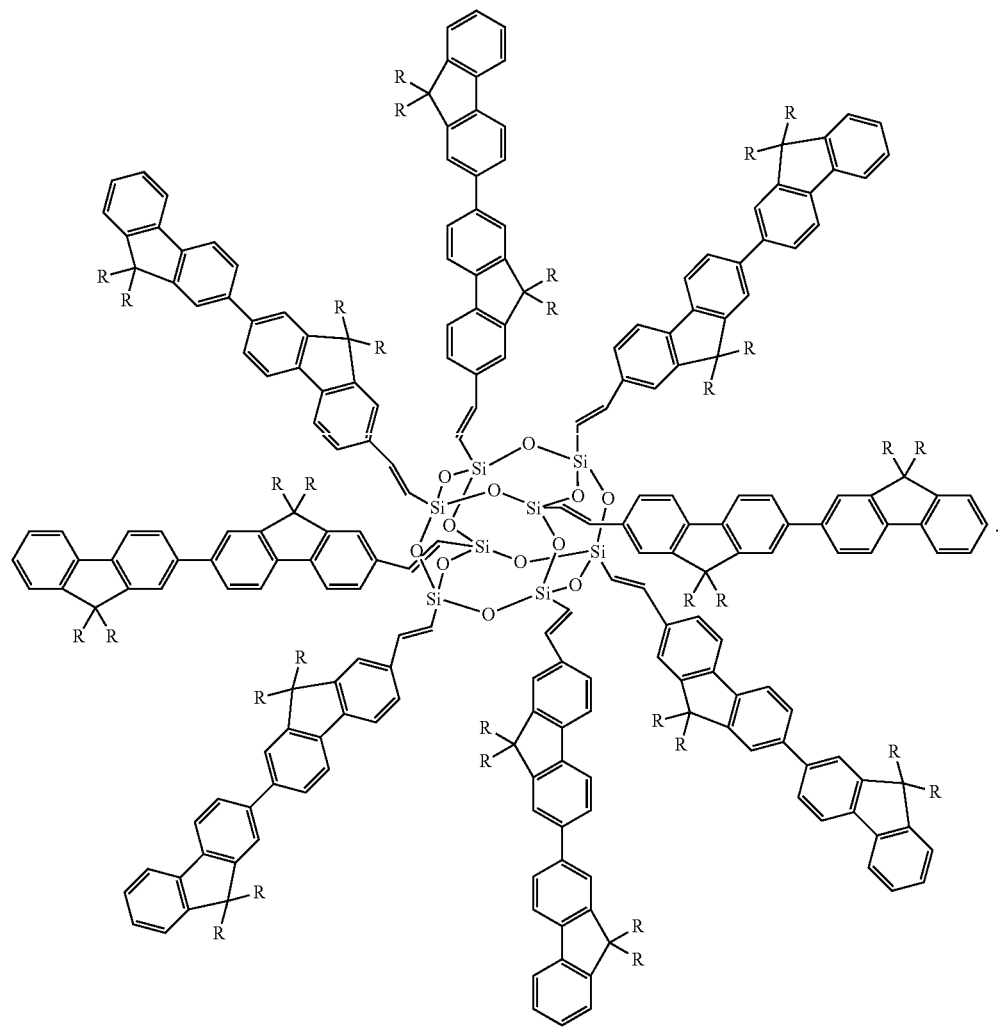
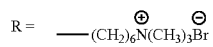

In another specific embodiment, compound is represented by the following structural formula:

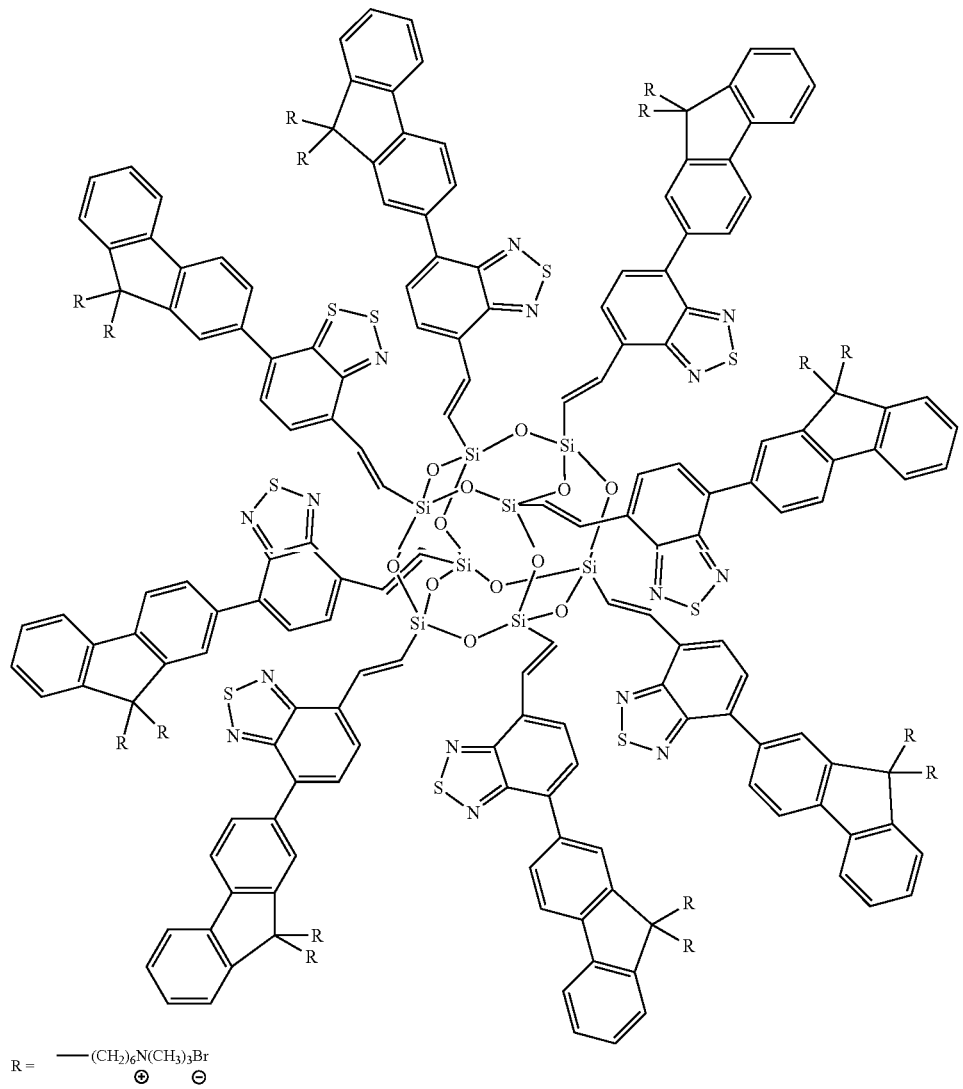

R = —(CH$_2$)$_6$N(CH$_3$)$_3$Br
       ⊕           ⊖

Another embodiment is a composition comprising a POSS compound and a carrier.

Another embodiment of this invention is a method of imaging the nucleus in a cell, comprising the steps of: exposing the cell to a POSS compound; allowing the POSS compound to bind the nucleus; and assaying the cell to determine the location of the POSS compound within or on the cell.

As used herein "assaying" refers to a determination of the quantity or location, or both of the POSS compound. "Visualizing" is a method of assaying.

As used herein a "cell" is any cell with a nucleus. Specifically, the cell is a eukaryotic cell.

The nucleus within a eukaryotic cell can be imaged by the use of POSS compounds of the invention in bioimaging of live, fixed cells or cell lysates derived thereof from fixed or dead cells. The method comprises the steps of exposing the cell to the POSS compound, allowing the POSS compound to accumulate within or on the cell, and visualizing the fluorescence emitted from the POSS compound. The fluorescence emitted can be assayed by techniques known to those of skill in the art and include, fluorescence, confocal microscopy and two photon fluorescence microscopy.

"Fluorescence spectroscopy", also known as "fluorometry" or "spectrofluorometry," is a type of electromagnetic spectroscopy which analyzes fluorescence from a sample. A beam of light, usually ultraviolet light, is used to excite the electrons in molecules of certain compounds, causing them to emit light of a lower energy, typically, but not necessarily, visible light.

Typically, fluorescence spectroscopy involves measurement of the different frequencies of fluorescent light that are emitted by a sample, while holding the excitation light at a constant wavelength.

"Two-Photon Fluorescence spectroscopy" is a type of fluorescence spectroscopy that relies on the quasi-simultaneous absorption of two or more photons (of either the same or different energy) by a molecule.

As used herein "exposing the cell to the POSS compound" means the cell and the POSS compound are present in the same container or in the same solution and may come into contact. Exposing the cell the POSS compound includes adding the POSS compound, either in solution or as a solid, to the culture media used to cultivate the cells.

In one embodiment of the invention, the cells are assayed using fluorescence spectroscopy. In a specific embodiment, the fluorescence spectroscopy is two photon fluorescence spectroscopy.

The POSS compounds of the invention can be can be designed and used to amplify the fluorescence signals of organic dyes (such as Fluorescein, Rhodamine, Texas red, Alexa Fluor, Cy3, Cy5, ethidium bromide, thiazole orange et al.), fluorescent proteins, and fluorescent nanomaterials (such as quantum dots, nanoclusters et al.). By choosing appropriate oligomers as the arm of the POSS based molecule, the spectral overlap between the emission of the POSS compound and the absorption of signaling molecule can be optimized to allow efficient energy transfer to amplify the signal output of the dye signals. FIG. 6 demonstrates the energy transfer between POSSFF and ethidium bromide in solution, which can amplify the ethidium bromide signal by a factor of 50.

Figure 11:
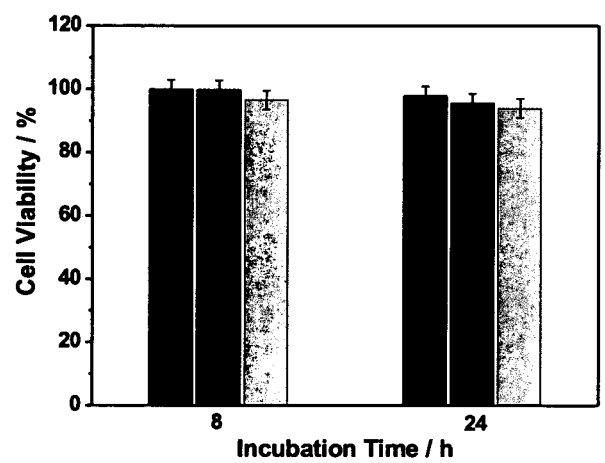
FIG. 11 is a bar graph depicting the in-vitro viability of NIH 3T3 cells treated with POSSFF solutions at the concentration of 0.01 (black), 0.02 (dark gray) or 0.1 mg/mL (light gray) for 8 and 24 h. The percentage cell viability of treated cells is calculated relative to that of untreated cells with a viability arbitrarily defined as 100%.

The water-soluble POSS-based fluorescent nanodots or nanoparticles can be used as stains for biosensing. For instance, they can stain the captured biomolecules on a certain surface (such as curved surfaces of nanoparticles, and plane surfaces of glass or quartz) via electrostatic interactions. The fluorescence of POSS-based nanodots is only observed in the presence of captured target. The linear relationship between the target on surface and the fluorescence of POSS-based nanodots also allows for precise quantification of the target. FIG. 11 is a schematic illustration of POSS-based label free protein detection. The method comprises the steps of exposing the nanoparticle to the POSS compound, and visualizing the fluorescence emitted from the POSS compound. The fluorescence emitted can be assayed by techniques known to those of skill in the art and include, fluorescence, confocal microscopy and two photon fluorescence microscopy.

One embodiment is a method of quantifiying a biomolecule, comprising the steps of: exposing the biomolecule to a polyhedral oligomeric silsesquioxane compound; allowing the polyhedral oligomeric silsesquioxane compound to bind to the biomolecule; and assaying the polyhedral oligomeric silsesquioxane compound, to quantify the biomolecule. In a specific embodiment of this method, the biomolecule is immobilized on a nanoparticle.

A method to detect a biological molecule, comprises the steps of immobilizing an aptamer on a solid support; incubating the immobilized aptamer with a test solution; exposing the test solution to a polyhedral oligomeric silsesquioxane compound; and measuring the fluorescence of the test solution, thereby detecting the biological molecule.

Aptamers are oligonucleic acid or peptide molecules that bind to a specific target molecule. More specifically, aptamers can be classified as: DNA or RNA aptamers, consisting of (usually short) strands of oligonucleotides or peptide aptamers, consisting of a short variable peptide domain, attached at both ends to a protein scaffold. An aptamer to be immobilized on the solid support is selected based upon its ability to bind the biological molecule of interest.

As used herein, a "test solution", is a solution that may or may not contain the biological molecule of interest. The presence and/or quantity of the biological molecule of interest may be detected by the method of this invention.

A "biomolecule" or "biological molecule" includes molecules associated with cells. For instance biomolecules include, but are not limited to, proteins, peptides, nucleic acids, lipids, sugars, biomarkers or any combination thereof.

A "biomarker," as used herein, is any substance with the specific binding with a certain biomolecue.

"Alkyl" used alone or as part of a larger moiety such as "alkoxy", refers to a straight or branched, saturated aliphatic group having the specified number of carbons, typically having 1 to 12 carbon atoms. More particularly, the aliphatic group may have 1 to 8, 1 to 6, or 1 to 4 carbon atoms. This term is exemplified by groups such as methyl, ethyl, n-propyl, isopropyl, n-butyl, isobutyl, tert-butyl, n-hexyl, and the like.

"Alkenyl" refers to a straight or branched aliphatic group with at least one double bond. Typically, alkenyl groups have from 2 to 12 carbon atoms, from 2 to 8, from 2 to 6, or from 2 to 4 carbon atoms. Examples of alkenyl groups include ethenyl (—CH═CH$_2$), n-2-propenyl (allyl, —CH$_2$CH═CH$_2$), pentenyl, hexenyl, and the like.

"Alkynyl" refers to a straight or branched aliphatic group having at least 1 site of alkynyl unsaturation. Typically, alkynyl groups contain 2 to 12, 2 to 8, 2 to 6 or 2 to 4 carbon atoms. Examples of alkynyl groups include ethynyl (—C≡CH), propargyl (—CH$_2$C≡CH), pentynyl, hexynyl, and the like.

"Alkenylene" refers to an alkylene group within which one carbon-carbon single bond is replaced with a double bond. For example, methylene, ethylene, propylene, and the like.

"Alkynylene" refers to an alkylene group within which one carbon-carbon single bond is replaced with a triple bond.

"Aryl" used alone or as part of a larger moiety as in "aralkyl" refers to an aromatic carbocyclic group of from 6 to 14 carbon atoms having a single ring or multiple condensed rings. The term "aryl" also includes aromatic carbocycle(s) fused to cycloalkyl or heterocycloalkyl groups. Examples of aryl groups include fluorene, benzene, biphenyl, pyridine, bipyridinium, triphenylamine, anthracene, thiophene, carbazole, and benzothiadiazole, and the like.

"Alkoxy" refers to the group —O—R where R is "alkyl", "cycloalkyl", "alkenyl", or "alkynyl". Examples of alkoxy groups include for example, methoxy, ethoxy, ethenoxy, and the like.

The compounds according to the present invention may be in free form or in the form of physiologically acceptable, non-toxic salts. These salts may be obtained by reacting the respective compounds with physiologically acceptable acids and bases.

Examples of such salts include but are not limited to hydrochloride, hydrobromide, hydroiodide, hydrofluoride. nitrate, sulfate, bisulfate, pyrosulfate, sulfite, bisulfite, phosphate, acid phosphate, monohydrogenphosphate, dihydrogenphosphate, metaphosphate, pyrophosphate, isonicotinate, acetate, trifluoroacetate, propionate, caprylate, isobutyrate, lactate, salicylate, citrate, tartrate, oxalate, malonate, suberate, sebacate, mandelate, chlorobenzoate, methylbenzoate, dinitrobenzoate, phthalate, phenylacetate, malate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminium, calcium, lithium, magnesium, potassium, sodium, zinc, and diethanolamine, N,N'-dibenzylethylenediamine, chloroprocaine, choline, dicyclohexylamine, ethylenediamine, N-methylglucamine, and procaine salts.

Exemplification

Example 1

Synthesis of POSSFF and POSSFBT

Synthesis of 2-(9,9-bis(6-bromohexyl)fluoren-2-yl)-4,4,5,5-tetramethyl-1,3,2-dioxaborolane (1). 2-Bromo-9,9-bis-(6- bromohexyl)fluorene (4.54 g, 7.95 mmol), bis(pi nacolatodiboron) (3.02 g, 11.93 mmol), and potassium acetate (2.94 g, 29.82 mmol) were placed in a 100-mL round bottom flask. Anhydrous dioxane (80 mL) and [PdCl2(dppf)] (0.20 g, 0.24 mmol) were added to the flask and the reaction vessel was degassed. The mixture was stirred at 80° C. for 12 h under nitrogen. After the mixture had been cooled to room temperature, dioxane was removed by rotary evaporation. The residue was extracted with dichloromethane, and the organic phase was washed with water and brine, and dried over magnesium sulfate. The solvent was removed and the residue was purified by silica gel column chromatography (dichloromethane/hexane=1:2) to afford 2.

Synthesis of 2,7-dibromo-9,9-bis(6-bromohexyl)fluorene (2). 2,7-Dibromofluorene (1.23 g, 5 mmol) was added to a mixture of aqueous potassium hydroxide (100 mL, 50 w %), tetrabutylammonium bromide (0.330 g, 1 mmol), and 1,2-bis(2-bromoethoxy)ethane (13.9 g, 50 mmol) at 75° C. After 15 min, the mixture was cooled to room temperature. After extraction with $CH_2Cl_2$, the combined organic layers were washed successively with water, aqueous HCl (1 M), water, and brine and then dried over $Na_2SO_4$. After removal of the solvent and the excess 1,2-bis(2-bromoethoxy)ethane; the residue was purified by silica gel column chromatography using hexane and dichloromethane (1:2) as the eluent, and recrystallized from ethanol and $CH_2Cl_2$ (5:1) to afford M2 as white needle crystals (1.50 g, 48.0%).

Synthesis of 2-(7-bromo-9,9-bis(6-bromohexyl)fluorenyl)-9,9-bis(6-bromohexyl)fluorene (3). 1 (2.84 g, 4.60 mmol), 2 (4.5 g, 6.9 mmol), $Pd(PPh_3)_4$ (53 mg, 0.046 mmol), potassium carbonate (4.43, 32.0 mmol) were placed in a 100 mL round bottom flask. A mixture of water (12 mL) and toluene (30 mL) was added to the flask and the reaction vessel was degassed. The mixture was vigorously stirred at 90° C. for 2 days. After it was cooled to room temperature, dichloromethane was added to the reaction mixture. The organic portion was separated and washed with brine before drying over anhydrous $MgSO_4$. The solvent was evaporated off, and the solid residues were purified by column chromatography on silica gel using dichloromethane/hexane (1:5) as eluent to afford 3.

Synthesis of 2-(7-bromo-bis(6-N,N,N-trimethylammonium)hexyl)fluorenyl)-bis(6-N,N,N-trimethylammonium)hexyl)fluorene (4). Condensed trimethylamine (~5 mL) was added dropwise to a solution of 3 (1 g, 0.94 mmol) in THF (10 mL) at −78° C. The mixture was allowed to warm to room temperature. The precipitate was redissolved by the addition of water (10 mL). After the mixture was cooled to −78° C., additional trimethylamine (~3 mL) was added. The mixture was stirred at room temperature for 24 h. After removal of the solvent, acetone was added to precipitate 4 (1.2 mg, 98%) as white powders.

Synthesis of 4-(9,9-bis(6-bromohexyl)-9H-fluoren-2-yl)-7-bromobenzothiadiazole (7). 2-(9,9-bis(6-bromohexyl)-fluoren-2-yl)-4,4,5,5-tetramethyl-1,3,2-dioxaborolane (6) (2.84 g, 4.60 mmol), 4,7-dibromobenzothiadiazole (2.16 g, 7.36 mmol), $Pd(PPh_3)_4$ (53 mg, 0.046 mmol), potassium carbonate (4.43, 32.0 mmol) were placed in a 100 mL round bottom flask. A mixture of water (12 mL) and toluene (30 mL) added to the flask and the reaction vessel was degassed. The mixture was vigorously stirred at 90° C. for 2 days. After it was cooled to room temperature, dichloromethane was added to the reaction mixture. The organic portion was separated and washed with brine before drying over anhydrous MgSO4. The solvent was evaporated off, and the solid residues were purified by column chromatography on silica gel using dichloromethane/hexane (1:5) as eluent to afford as grassy liquid. $^1$H NMR (500 MHz, $CD_3OD$, δ ppm): 8.0-7.87 (m, 3 H), 7.85 (d, 1 H, J=7.84), 7.77 (d, 1 H, J=7.26), 7.66 (d, 1 H, J=7.57), 7.45-7.30 (m, 3 H), 3.27 (t, 4 H, J=6.84, 6.84), 2.14-1.97 (m, 4 H), 1.74-1.62 (m, 4 H), 1.32-1.18 (m, 4 H), 1.17-1.04 (m, 4 H), 0.83-0.66 (m, 4 H). $^{13}$C NMR (125 MHz, $CD_3OD$, δ ppm): 154.00, 153.35, 152.83, 150.90, 141.76, 140.50, 135.37, 134.49, 132.31, 128.24, 128.05, 127.58, 127.08, 123.79, 122.91, 120.13, 119.89, 112.81, 55.16, 40.12, 33.92, 32.60, 29.04, 27.73, 23.61. MS (MALDI-TOF): m/z 707.37 [M]$^+$.

Synthesis of 4-(9,9-bis(6-N,N,N-trimethylammonium)hexyl)fluorenyl)-7-bromobenzothiadiazole (8). Synthesis of Condensed trimethylamine (~5 mL) was added dropwise to a solution of 2 (1 g, 0.94 mmol) in THF (10 mL) at −78° C. The mixture was allowed to warm to room temperature. The precipitate was redissolved by the addition of water (10 mL). After the mixture was cooled to −78° C., additional trimethylamine (~3 mL) was added. The mixture was stirred at room temperature for 24 h. After removal of the solvent, acetone was added to precipitate 3 (1.4 mg, 99%) as yellow powders. $^1$H NMR (500 MHz, $CD_3OD$, δ ppm): 8.38-8.26 (m, 2 H), 8.26-8.19 (m, 1 H), 8.19-8.12 (m, 1), 8.12-8.00 (m, 2 H), 7.79-7.56 (m, 3 H), 3.53-3.42 (m, 4 H), 3.09 (3, 18 H), 2.55-2.42 (m, 4 H), 1.95-1.72 (m, 4 H), 1.53-1.31 (m, 8 H), 1.12-0.78 (m, 4H). ($^{13}$C NMR (125 MHz, $CD_3OD$, δ ppm): 155.28, 154.50, 152.26, 152.055, 143.31, 142.18, 136.97, 135.38, 134.03, 129.73, 128.93, 128.46, 125.18, 124.33, 121.35, 121.05, 113.78, 67.81, 55.58, 53.68, 41.19, 30.35, 26.98, 24.92, 23.75.

Synthesis of POSSFF. Octavinyl POSS (5) (11.4 mg, 0.018 mmol), 4 (187 mg, 0.144 mmol), $Pd(OAc)_2$ (3.2 mg, 14.4 µmol), and $P(o-tolyl)_3$ (24 mg, 78.4 µmol) were placed in a 25 mL round bottom flask. A mixture of DMF (1 mL), and triethylamine (0.5 mL) was added to the flask and the reaction vessel was degassed. The mixture was vigorously stirred at 100° C. for 36 h. It was then filtered and the filtrate was poured into acetone. The precipitate was collected and washed with acetone, and was redissolved in water. The solution was filtered through a 0.22 µm syringe driven filter to give limpid solution. Finally, the product was purified by dialysis against Milli-Q water using a 3.5 kDa molecular weight cutoff dialysis membrane for 5 days. After freeze-drying, POSSFF (74 mg, 45%) was obtained as light yellow powders.

Synthesis of POSSFBT. Octavinyl POSS (5) (11.4 mg, 0.018 mmol), 8 (119 mg, 0.144 mmol), $Pd(OAc)_2$ (3.2 mg, 14.4 µmol), and $P(o-tolyl)_3$ (24 mg, 78.4 µmol) were placed in a 25 mL round bottom flask. A mixture of DMF (1 mL), and triethylamine (0.5 mL) was added to the flask and the reaction vessel was degassed. The mixture was vigorously stirred at 110° C. for 36 h. It was then filtered and the filtrate was poured into acetone. The precipitate was collected and washed with acetone, and was redissolved in water. The solution was filtered through a 0.22 µm syringe driven filter to give limpid solution. Finally, the product was purified by dialysis against. Milli-Q water using a 3.5 kDa molecular weight cutoff dialysis membrane for 5 days. After freeze-drying, POSSBT (96 mg, 73%) was obtained as yellow fibers. $^1$H NMR (500 MHz, $CD_3OD$, δ ppm): 8.47 (s, 1 H), 8.43 (d, 2 H), 8.31 (d, 1 H), 8.25 (d, 2 H), 7.74-7.76 (m, 2 H), 7.83-7.74 (m, 1 H), 7.74-7.63 (m, 2 H), 3) 3.54-3.38 (m, 4 H), 3.09 (s, 18 H), 2.57-2.39 (m, 4 H), 1.95-1.80 (m, 4 H), 1.54-1.40 (m, 8 H), 1.13-0.95 (m, 4 H).

This unimolecular nanoparticle has a good water-solubility (~0.23 mg/mL at 24° C.), as a result of its high charge density on its nanoglobular surface. The morphology and size of POSSFBT were studied by high-resolution transmission electron microscopy (HR-TEM). Spherical nanoparticles with an average diameter of 3.3±0.5 nm were observed, which coincides well with the single-molecular size of POSSFBT.

POSS compounds containing catonic, anionic or neutral R groups on either Ar or Ar' can be synthesized by the similar method as that used to synthesize POSSFF and POSSFBT.

Example 2a

Optical Properties of POSSFF and POSSFBT

Figure 5:
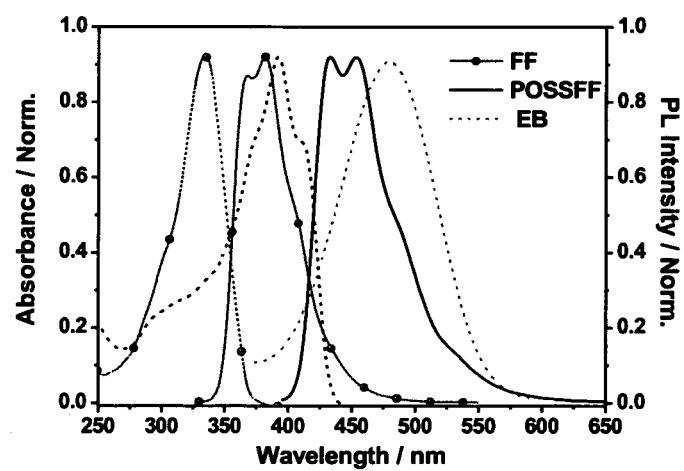
FIG. 5 is the Normalized UV-vis absorption spectra of fluorene dimer (FF), POSSFF and ethidium bromide (EB) (dashed lines), and photoluminescence (PL) spectra of FF and POSSFF (solid line) in water. Excitation at the absorption maximum.
Figures 8A, 8B, 8C, 8D:
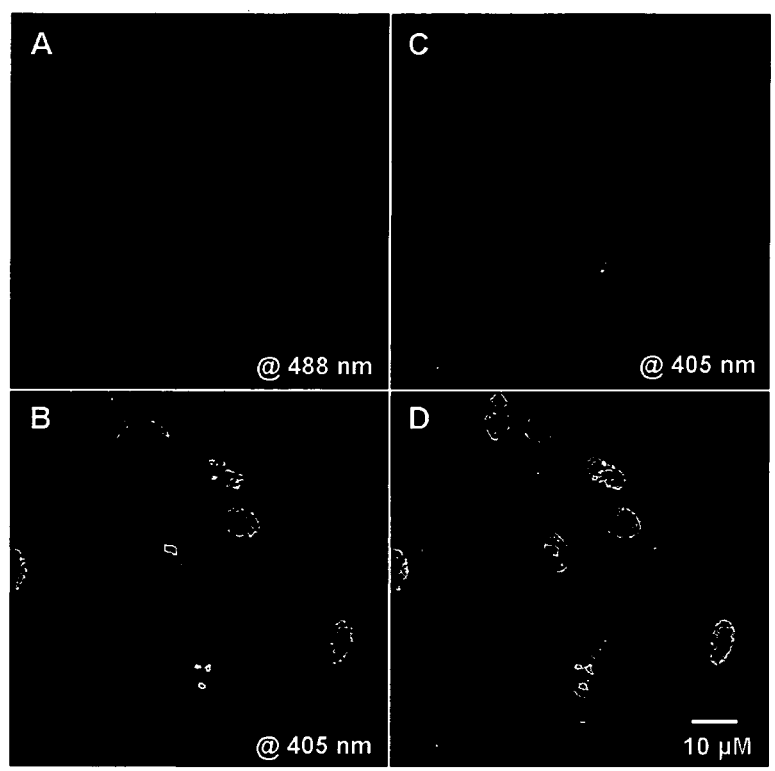
FIG. 8A-D are confocal laser scanning microscopy (CLSM) images taken of breast cancer cells (MCF-7) demonstrating the use of POSSFF as a signal amplifier.

The optical properties of POSSFF in water and in buffer were examined. As shown in FIG. 5, the absorption and emission maxima of POSSFF are 390 and 433 nm, respectively. The photoluminescence (PL) quantum yields of POSSFF is 0.85, measured using quinine sulfate in 0.1 M $H_2SO_4$ (quantum yield=0.55) as the standard. Moreover, the quantum yields of POSSFF in 150 mM phosphate-buffer saline (PBS, pH=7.4) are 0.80. The extremely strong and ionic-resistant fluorescence makes POSSFF a perfect energy donor for optical amplification in biological applications.

Example 2b

Signal Amplification Using POSSFF and POSSFBT

The capability of POSSFF as an energy donor to amplify the signal of ethidium bromide (EB) through FRET was evaluated. Energy transfer experiments were conducted in 25 nM PBS at [EB]=2 μM and [ssDNA] or [dsDNA]=2 nM. In the absence of POSSFF, the PL intensity of EB/dsDNA upon direct excitation of EB at 475 nm was 2.5-fold of that of free EB, and was nearly the same as that of free EB for EB/ssDNA. Upon addition of POSSFF into EB/DNA solution, the fluorescent signal of EB/DNA upon excitation at 390 nm was collected at 610 nm.

FIG. 6A summarizes the FRET-induced PL intensity of EB/DNA as a function of donor concentration. With increasing [POSSFF], the PL intensity at 610 nm significantly increased for EB/dsDNA, while it slightly changed for EB/ssDNA. The saturation occurs at [POSSFF]=1.4 μg mL$^{-1}$.

The PL spectra at the saturation point are depicted in FIG. 6B. For EB/dsDNA/POSSFF, two emission bands centered at 443 and 610 nm are observed corresponding to the fluorescence of POSSFF and EB, respectively. The PL intensity of EB/dsDNA/POSSFF at 610 nm is 52-fold of that of EB/dsDNA. In contrast, only the emission band of POSSFF is present for EB/ssDNA/POSSFF, and its PL intensity at 610 nm is similar to that of EB/ssDNA. As a result of the discrepancy in the signal amplification and spectral profiles, naked-eye discrimination of dsDNA from ssDNA in the presence of POSSFF becomes feasible.

Photographs of the fluorescent solutions of EB/ssDNA and EB/dsDNA in the absence and presence of 1.4 μg mL$^{-1}$ POSSFF under 365 nm UV radiation are shown in FIG. 6C. [DNA]=20 nM and [EB]=2 μM were taken. The photographs show that the fluorescence of EB/DNA solutions is very weak in the absence of POSSFF, while strong blue and pink fluorescence are observed in the presence of POSSFF for EB/ssDNA and EB/dsDNA solutions, respectively.

The linear optical spectra of POSSFBT in water are shown in FIG. 7A-D. POSSFBT has two absorption peaks at 320 and 468 nm with the emission maximum at 650 nm. The PL quantum yield of POSSFBT is low (1% in water), which can be substantially increased upon interaction with DNA to ~10%. In addition, POSSFBT could be excited at 900 nm (two-photon absorption), which can be used for multiphoton imaging.

The one-photon fluorescence response of POSSFBT towards nucleic acid is investigated in 25 mM phosphate-buffer saline (PBS, pH=7.4) at [POSSFBT]=2 μM. As depicted in FIG. 7B, addition of DNA into the solution induces a progressive intensity increase in the emission of POSSFBT. The saturation occurs at [DNA]=3.2 μM, where the emission intensity of POSSFBT at 610 nm is ~6.7 fold higher than that in the absence of DNA. Therefore, the dark fluorescence of POSSFBT is substantially turned-on by DNA, leading to bright orangered fluorescence (inset of FIG. 7B). The light-up response of POSSFBT toward DNA results from the complexation between oppositely-charged POSSFBT and DNA via electrostatic attractions, which in turn creates a hydrophobic environment to reduce the contact between the polarity-sensitive arm of POSSFBT and water molecules.

The TPA cross sections ($\sigma_2$) of POSSFBT in the absence and presence of DNA were investigated by two-photon excited fluorescence (TPEF) technique using a femtosecond pulsed laser source and Rhodamine 6G as the reference. Because of the laser limitation, $\sigma_2$ was measured from 630 to 770 nm. The TPA spectrum of POSSFBT in water reveals that $\sigma_2$ reaches a maximum of 126 GM at 760 nm within the detected range (FIG. 7C), which is comparatively large among the existing water-soluble TPA chromophores. The TPEF of 2 μM POSSFBT toward DNA in 25 mM PBS was then probed upon excitation at 760 nm. As shown in FIG. 7D, the TPEF of POSSFBT has an emission maximum at 608 nm, and its intensity increases by ~12.7 fold in the presence of 3.2 μM DNA relative to that in the absence of DNA. In fact, the $\sigma_2$ and $\sigma_2\Phi$ of POSSFBT/DNA at 760 nm are 220 and 145 GM, which are respectively ~1.7 and 11.5 fold larger than those of POSSFBT alone. Similar to its one-photon fluorescent behavior, the DNA-enhanced TPA of POSSFBT is ascribed to the reduction in the hydrophilicity of chromophore microenvironment upon complexation. The DNA-induced enhancement in the TPEF of POSSFBT (~12.7 fold) is considerably larger than that in its one-photon fluorescence (~6.7 fold), reflecting that utilization of TPEF in cellular imaging would have a better contrast.

Example 3

Cell Imaging with POSSFF and POSSFBT

Cell imaging with POSSFF as signal amplifier was examined using breast cancer cells (MCF-7) as an example. After incubation with POSSFF solution (0.1 μg/mL) and EB solution (1 μM) for 2 h, MCF-7 cells were fixed for fluorescent imaging studies. The excitation wavelengths are 405 and 488 nm, and the fluorescent signals are collected at the ranges of 430 to 470 nm and above 650 nm, respectively. The confocal laser scanning microscopy (CLSM) images were taken. The fluorescent image upon excitation of EB itself at 488 nm is dark. In contrast, excitation of POSSFF at 405 nm gives rise to bright and clear images. These data show that POSSFF is efficient donor molecule for amplified cell imaging (FIG. 8A-D).

Figures 9A, 9B, 9C, 9D:
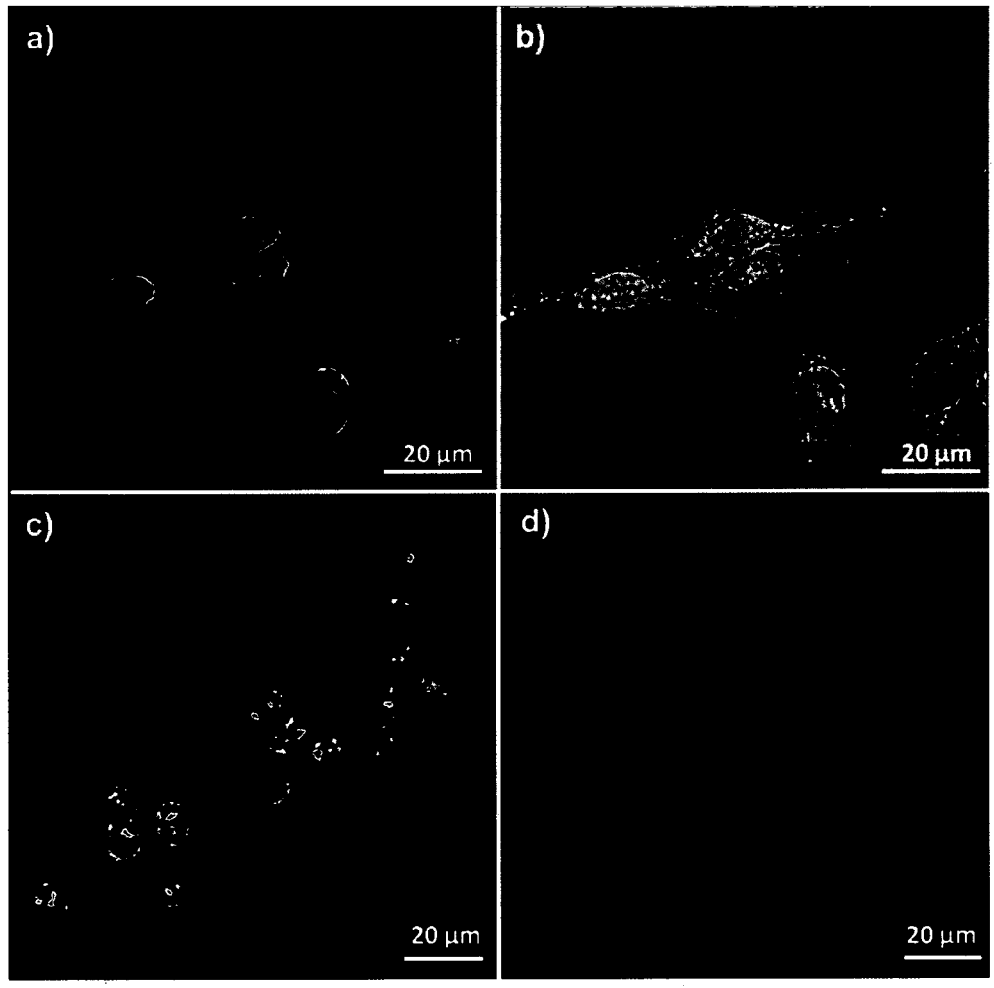
FIG. 9A-B are (A) OPEF and (B) OPEF/transmission overlapped images of MCF-cells stained with 1 µM POSSFBT. The signals are collected above 560 nm upon excitation at 488 nm.
FIGS. 9C and D are TPEF images of MCF-7 cells incubated with 1 µM POSSFBT (C) or SG (D) for 2 h. The signals are collected above 560 nm upon excitation at 760 nm.

One-photon and two-photo fluorescent cellular imaging (FIG. 9A-D) based on POSSFBT was investigated and compared using breast cancer cells (MCF-7). After incubation of MCF-7 cells with 1 μM POSSFBT for 2 h, the cells were fixed for imaging experiments. One-photon and two-photon fluorescence images of the MCF-7 cells were then obtained. The fluorescence signals are collected above 560 nm upon excitation at 488 and 760 nm, respectively. One-photon fluorescence imaging upon excitation at 488 nm demonstrated that POSSFBT is efficiently internalized by the cells, and enters the nuclei (FIG. 9A,B). The nuclei permeability of POSSFBT benefits from its small particle size (3.3 nm) within the effective transportation diameter of the nuclear pore complex (~9 nm), consequently allowing POSSFBT to traverse the NPC by passive diffusion. In addition, the fluorescence intensity in the nuclei is higher than that in the cytoplasm, due to the presence of a large amount of DNA in the nuclei that can substantially enhance the fluorescence of POSSFBT. In contrast, two-photon fluorescence imaging upon excitation at 760 nm shows that only the nuclei are indicated by the fluorescence of POSSFBT (FIG. 9C,D); furthermore, the strongest fluorescence is focused on the nucleoli where the nucleic acid concentration is highest in cell. These data reveal that two-photon fluorescence of POSSFBT is more effective in visualizing the nucleus structure than one-photon fluorescence does, which originates from the higher two-photon fluorescence response of POSSFBT toward DNA relative to its one-photon fluorescence.

The spherical surface of POSS and DNA-enhanced fluorescence of a COE to construct a nucleus-permeable unimolecular nanoparticle has advantages for two-photon fluorescent nucleus imaging. Comparison investigation reveals that two-photon fluorescence of POSSFBT outperforms one-photon fluorescence in nucleus imaging, as a result of the higher intensity enhancement of TPEF toward DNA relative to that of one-photon fluorescence. The compounds of the invention are effective nanomaterials for bioimaging to elucidates targeted gene/drug delivery to nucleus.

Example 4

Comparison with the Commercial Dye

The one-photon excited fluorescence (OPEF) and two-photon excited fluorescence (TPEF) cellular imaging based on POSSFBT was also compared with that for SYBR Green I (SG). SG is so far the most sensitive commercial dsDNA stain that easily penetrates living cells, allowing for TPEF cellular nucleus imaging (See I. M. Mackay, K. E. Arden, A. Nitsche, *Nucleic Acids Res.* 2002, 30, 1292, the entire teachings of which are incorporated herein by reference.)

After incubation of the cells with POSSFBT or SG at the dye concentration of 1, 0.1 and 0.02 μM for 2 h, the cells were fixed for confocal laser scanning microscopy (CLSM) experiments. OPEF imaging was obtained by excitation of the cells at 488 nm and collection of fluorescence above 560 nm under the fixed parameters. Comparison of the fluorescence image in FIG. 10A and the fluorescence/transmission overlapped image in FIG. 10B clearly indicates that POSSFBT is efficiently internalized by cells, and accumulates in the nuclei. The nucleus permeability of POSSFBT benefits from its rigid spherical shape and small particle size (~3.3 nm) that is within the effective transportation diameter of the nuclear pore complex (~9 nm). In addition, the strong fluorescence from the nuclei is ascribed to the presence of a large amount of nucleic acids (including dsDNA and RNA) and their complexes with proteins in the nuclei that can substantially enhance the fluorescence of POSSFBT. In contrast to the homogenously-stained nucleus pattern of SG (FIG. 10D), the brightness of nucleolus in POSSFBT-stained image is slightly higher than that of nucleoplasm. This difference should be caused by the fact that SG only shows strong light-up response toward dsDNA, while POSSFBT shows equally strong light-up response towards dsDNA and RNA. As nucleolus is the site of ribosomal RNA synthesis, it has the highest concentration of RNA in nucleus. Thereby, different from SG, POSSFBT highlights the cellular nucleolus more as compared to other parts of the nucleus. This deduction is further supported by the similar nucleus imaging pattern of SYTO 9 which is a general nucleic acid dye that shows nearly equal light-up responses toward dsDNA and RNA.

For TPEF imaging, the dye concentrations are fixed at 1 μM, and the cellular images were acquired by excitation of the cells at near-infrared wavelength (760 nm) and collection of signals above 560 nm. As shown in FIG. 10C, the TPEF imaging pattern of POSSFBT is similar to that for one-photon excited fluorescence (OPEF), as shown in FIG. 10A, while the fluorescence contrast between the nucleoli and the nucleoplasm is sharper for the TPEF image. In contrast, utilization of SG as TPEF stain does not provide a clear cellular image under the same experimental conditions (FIG. 10D) due to its low TPA cross section. Furthermore, when excited at the TPA maximum of SG (800 nm), the TPEF intensity of SG stained image remains nearly the same as that for FIG. 10D. These data highlight that the large TPA action cross section (ηδ) of POSSFBT in the presence of nucleic acids makes it superior over SG for TPEF imaging of cellular nucleus.

Example 5

Cytotoxicity

The cytotoxicity of POSSFBT was also evaluated for mouse embryonic fibroblast cells (NIH 3T3) using methylthiazolyldiphenyl-tetrazolium (MTT) cell-viability assay. FIG. 11 summarizes the in-vitro NIH 3T3 cell viability after being cultured with the nanosphere solutions at the concentration of 0.01, 0.02 or 0.1 mg/mL for 8 or 24 h. Within the tested period, the cell viabilities are close to 100%, indicating the low cytotoxicity of POSSFF and its applicability in long-term clinical applications. POSSFBT has shown similar results in cytotoxicity study.

Example 6

Nanoparticle Based Assay Platform for Lysozyme Detection

Figure 12:
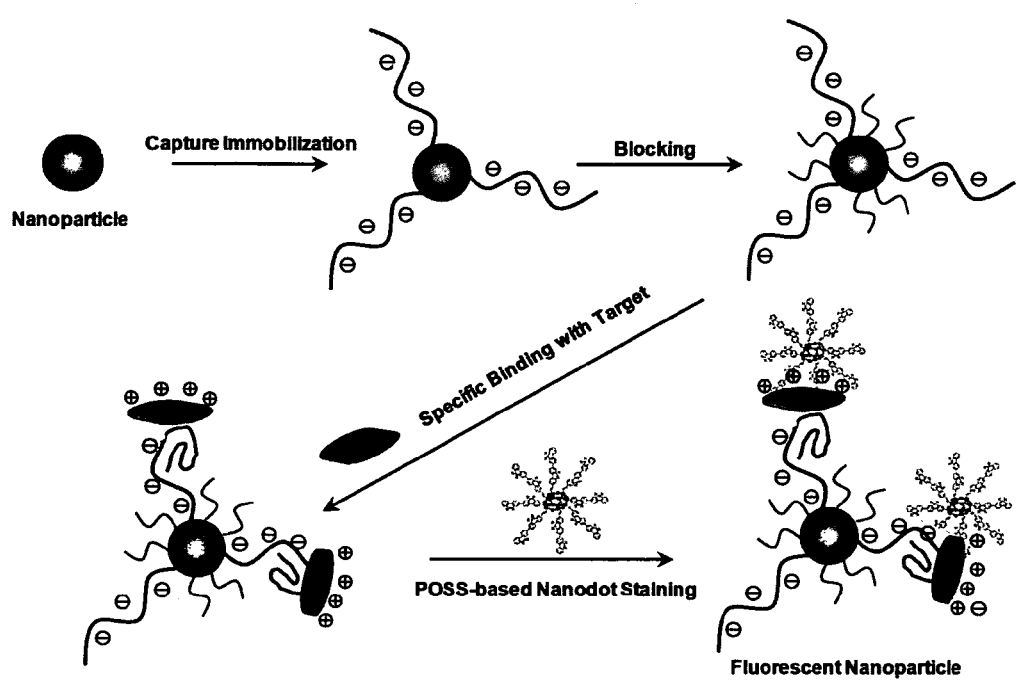
FIG. 12 is a schematic illustration of POSS-based label free protein detection.

As illustrated in FIG. 12, one starts with 100 nm silica nanoparticles (NPs) in solution. Immobilization of NPs with negatively charged anti-protein aptamers (Apt) yields Apt-NPs with various surface densities. These NPs can be further treated with ethanolamine to generate blocked Apt-NPs. Lysozyme can be used as an example biomolecue. Lysozyme has an isoelectric point (pI) of ~11.0, it is positively charged at neutral pH. Upon incubation with lysozyme, the blocked Apt-NPs undergoes a change in surface charge from negative to partially positive due to the recognition binding between the aptamer on NP surface and lysozyme. In the last step, addition of anionic functionalized POSS molecules to the solution yields POSS/lysozyme/Apt complexes on NP surface, giving rise to fluorescent NPs after removing excess of POSS molecules via centrifugation/redispersion of NPs and washing. On the contrary, since no recognition takes place between the aptamer and non-specific proteins, the surface charge on Apt-NPs remains negative, and no stain will occur. As such, label free protein detection can be realized by taking advantage of recognition-induced switching of surface charge of aptamers and subsequent stain.

While this invention has been particularly shown and described with references to example embodiments thereof, it will be understood by those skilled in the art that various changes in form and details, may be made therein without departing from the scope of the invention encompassed by the appended claims.

References (1) Burke, B.; Stewart, C. L. *Annu. Rev. Genom. Human Genet.* 2006, 7, 369-405.
(2) (a) Lichtman, J. W.; Conchello, J. A. *Nat. Methods* 2005, 2, 910-919. (b) Matzke, M. A.; Birchler, J. A. *Nat. Rev. Genet.* 2005, 6, 24-35
(3) Terai, T.; Nagano, T. *Curr. Opin. Chem. Biol.* 2008, 12, 515-521.
(4) (a) So, P. T. C.; Dong, C. Y.; Masters, B. R.; Berland, K. M. *Annu. Rev. Biomed. Eng.* 2000, 2, 399-429. (b) He, G. S.; Tan, L. S.; Zheng, Q.; Prasad, P. N. *Chem. Rev.* 2008, 108, 1245-1330
(5) Pouton, C. W.; Wagstaff, K. M.; Roth, D. M. *Adv. Drug Deliv. Rev.* 2007, 59, 698-717.
(6) Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. *Science* 2005, 307, 538-544.
(7) (a) Medintz, I. L.; Uyede, H. T.; Goldman, E. R.; Mattoussi, H. *Nat. Mater.* 2005, 4, 435-446. (b) Zheng, Y.; Gao, S.; Ying, J. Y. *Adv. Mater.* 2007, 19, 376-380.
(8) Lakowicz, J. R. Principles of Fluorescence Spectroscopy, 3$^{rd}$ ed.; Springer Science R Business Media, LLC: New York, 2006.
(9) Pu, K. Y.; Liu, B. *Adv. Funct. Mater.* 2009, 19, 277-284.
(10) (a) Woo, H. Y.; Korystov, D.; Mikhailovsky, A.; Nguyen, T. Q.; Bazan, G. C. *J. Am. Chem. Soc.* 2005, 127, 13794-13795. (b) Fang, Z.; Zhang, X.; Liu B. *Chem. Commun.* 2009, 920-922.

What is claimed is:

1. A compound represented by the following structural formula:

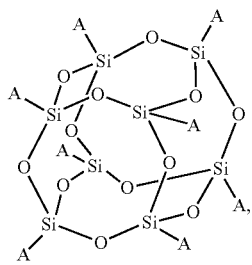

or an acceptable salt thereof, wherein:
each A is a group independently selected from the following structural formulae:

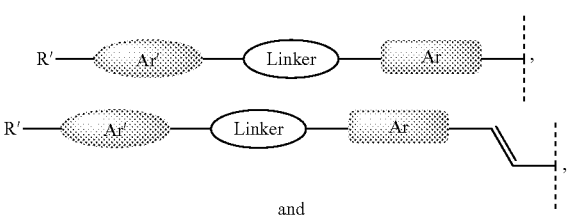

and

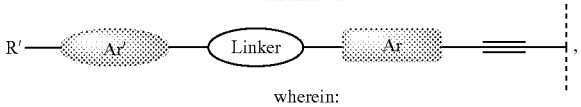

wherein:

each

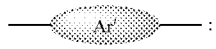

is independently selected from:

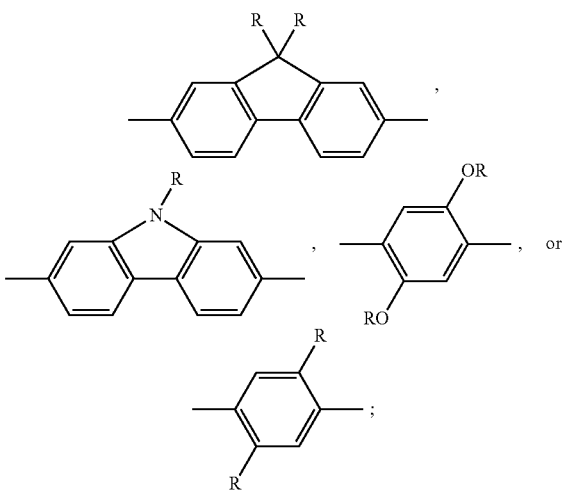

each Ar is independently an optionally substituted aromatic group;
each R is independently a cationic or anionic alkyl group, or a cationic or anionic oligo(ethylene oxide) group, or a cationic or anionic poly(ethylene oxide) group;
each Linker is a single bond, double bond, triple bond, —$CH_2$—, or —$CH_2CH_2$—; and
each R' is independently H or a terminal reactive group.

2. The compound of claim 1, wherein the cationic alkyl group is —$(CH_2)_n NMe_3 X$, where n=3-13; the cationic oligo (ethylene oxide) group is —$(CH_2CH_2O)_n NMe_3 X$, where n=2-100; wherein X for both —$(CH_2)_n NMe_3 X$ and —$(CH_2CH_2O)_n NMe_3 X$ is selected from $Br^-$, $I^-$, $BF_4^-$, $CF_3SO_3^-$, ammonium hexafluorophosphate, and tetrakis[3,5-bis(trifluoromethyl)phenyl] borate.

3. The compound of claim 1, wherein:
the anionic alkyl group is —$(CH_2)_n$ X' and the anionic oligo(ethylene oxide) or poly(ethylene oxide) group is —$(CH_2CH_2O)_n$ X'; wherein for both —$(CH_2)_n$ X' and —$(CH_2CH_2O)_n$X':
X' is selected from $SO_3^{2-}Y_2$, $PO_3^{2-}Y_2$, and $CO_2^-Y$;
Y is selected from $Na^+$ and $K^+$; and
n is 3-100.

4. The compound of claim 1, wherein the terminal reactive group is selected from COOH, $NH_2$, CHO and SH.

5. A compound represented by the following structural formula:

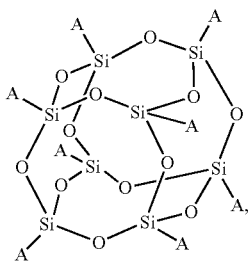

or an acceptable salt thereof, wherein:

each A is a group independently selected from the following structural formulae:

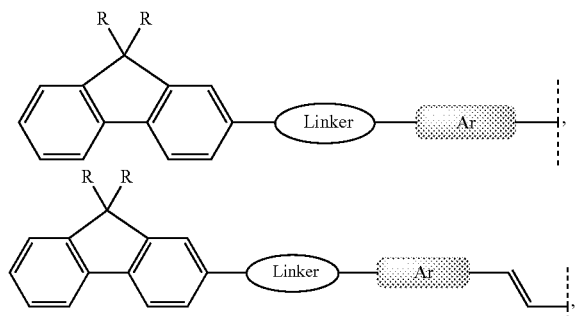

and

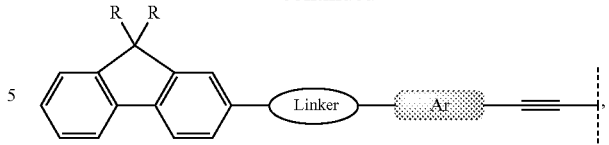

wherein:

Ar is an optionally substituted aromatic group;
Linker is a single bond, double bond, triple bond, $-CR^1_m-$; wherein $R^1$ is hydrogen, a halogen, a hydroxy group, an amino group, a $C_1$-$C_6$ alkyl group, a $C_2$-$C_6$ alkenyl group, a $C_2$-$C_6$ alkynyl group, or a $C_1$-$C_6$ alkoxy group; wherein the alkyl, alkenyl, alkynyl, or alkoxy groups may be optionally substituted with a halogen, a hydroxy group, a $C_1$-$C_4$ alkoxy goup, or an amino group, wherein m is 1 or 2; and
each R is independently hydrogen, a cationic alkyl side group, a cationic oligo(ethylene oxide) group or a cationic poly(ethylene oxide) group, provided that at least one R is not hydrdogen.

6. The compound of claim 5, wherein Ar is selected from the group consisting of fluorene, benzene, biphenyl, pyridine, bipyridinium, triphenylamine, anthracene, thiophene, carbazole, and benzothiadiazole.

7. The compound of claim 5, wherein each R is independently selected from the group consisting of hydrogen, $-(CH_2)_n NMe_3 X$ and $-(CH_7CH_2O)_n NMe_3 X$; wherein X is an anionic counterion and n is 3 to 13.

8. The compound of claim 7, wherein X is selected from $Br^-$, $I^-$, $BF_4^-$, $CF_3SO_3^-$, ammonium hexafluorophosphate, and tetrakis[3,5-bis(trifluoromethyl)phenyl]borate.

9. The compound of claim 5, wherein the compound is

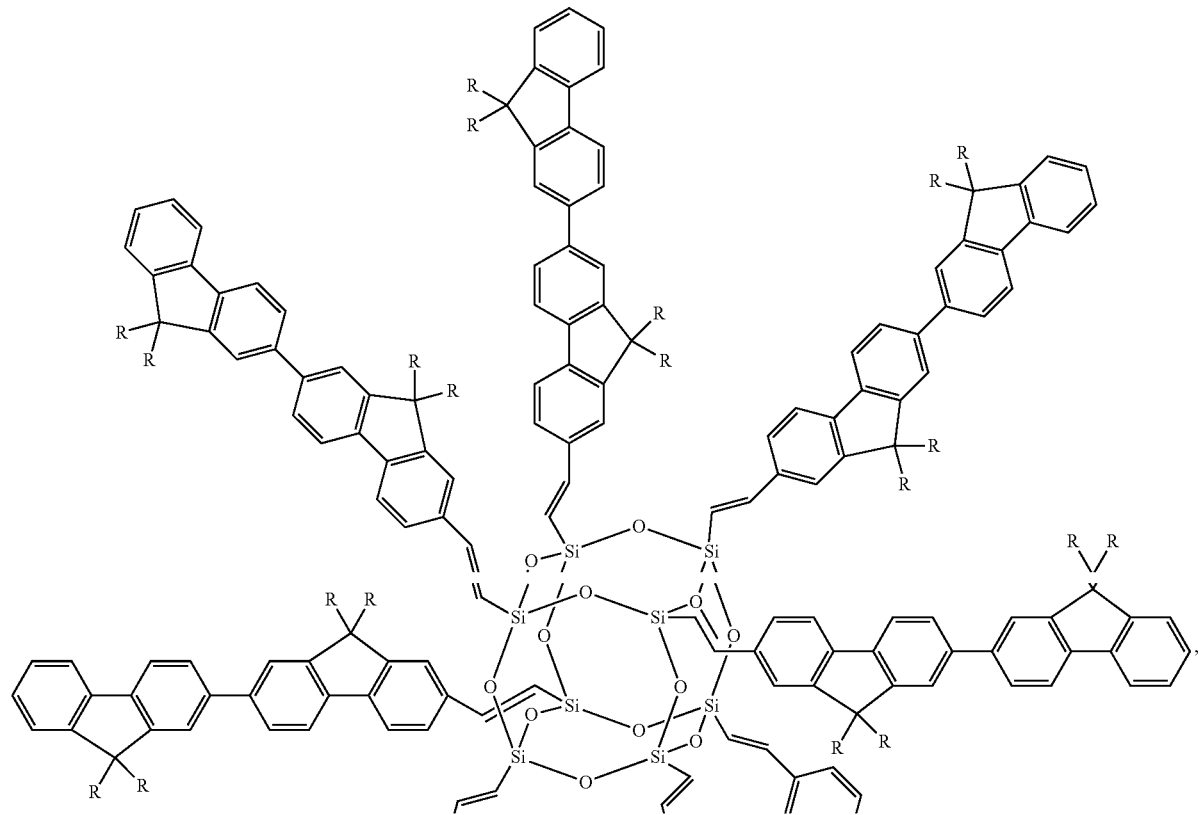

29
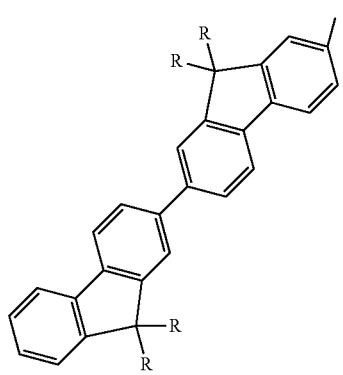
-continued
30
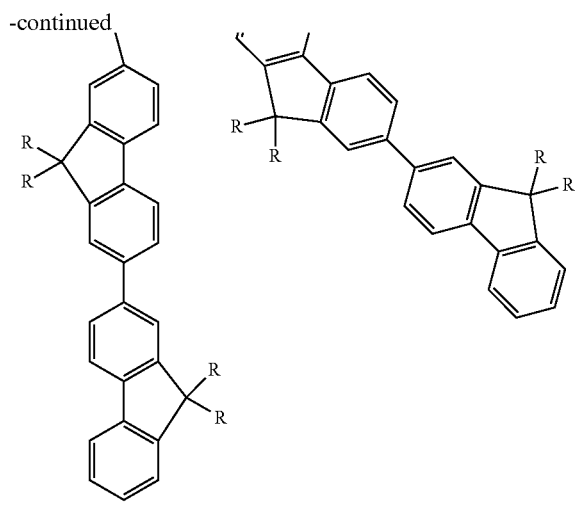
or
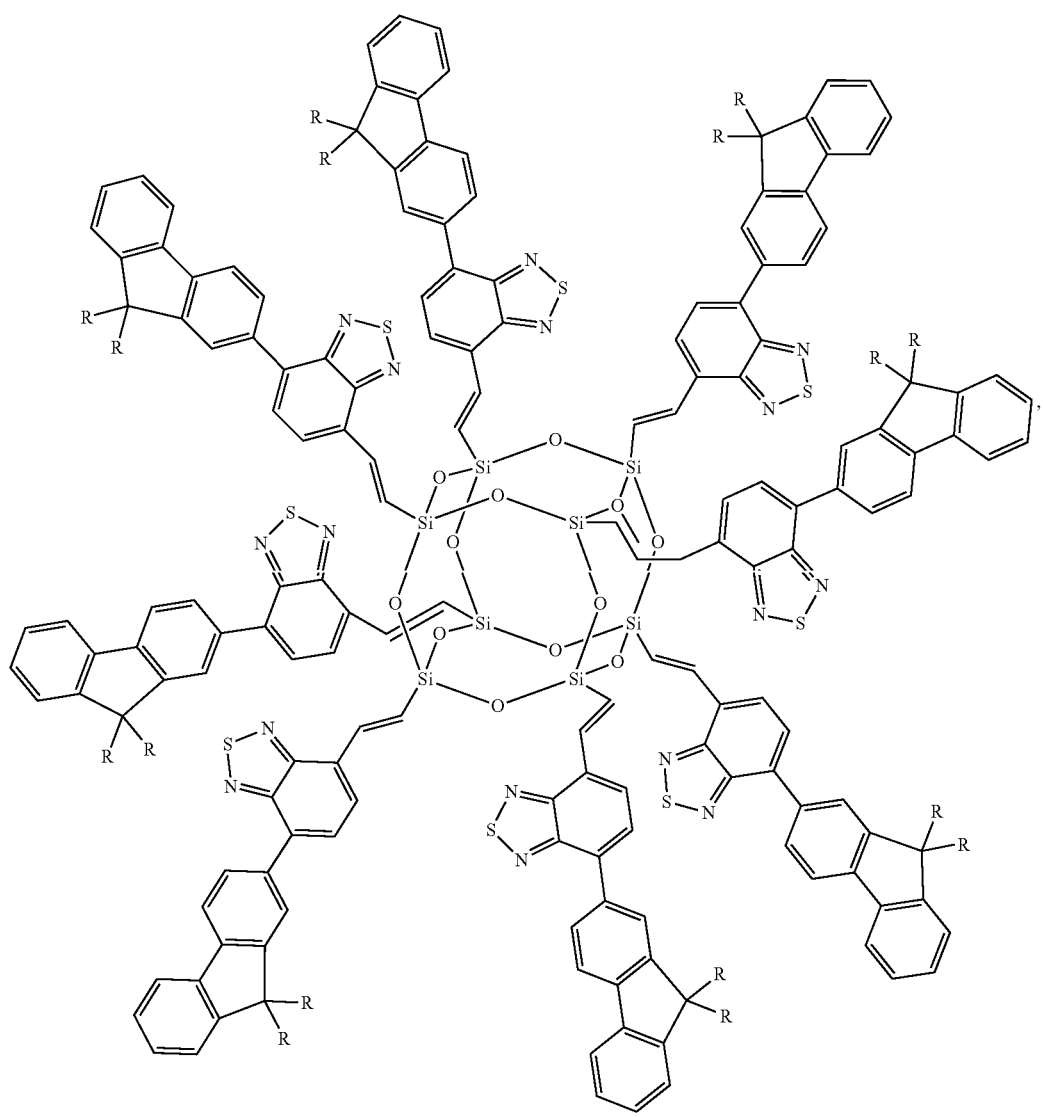
wherein R represents —$(CH_2)_6N^+(CH_3)_3Br^{31}$ .

10. A compound represented by the following structural formula:

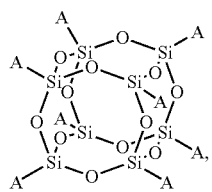

or an acceptable salt thereof, wherein:

each A is a group independently selected from the following structural formulae:

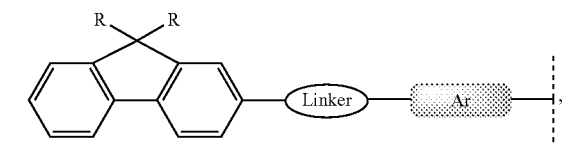

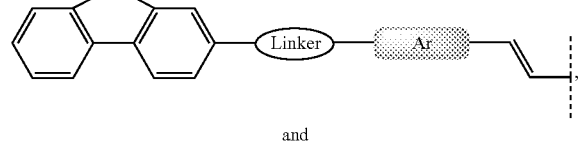

and

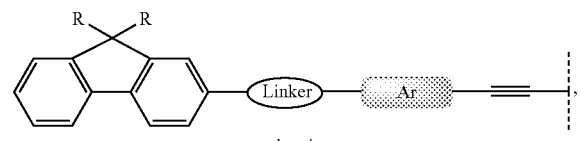

wherein:

Ar is an optionally substituted aromatic group;

each Linker is a single bond, double bond, triple bond, —CH$_2$—, or —CH$_2$CH$_2$—; and each R is independently hydrogen, a cationic alkyl side group, a cationic oligo(ethylene oxide) group, or a cationic poly(ethylene oxide) group, provided that at least one R is not hydrogen.

11. The compound of claim 10, wherein the cationic alkyl group is —(CH$_2$)$_n$NMe$_3$X, where n=3–13-); the cationic oligo(ethylene oxide) group or cationic poly(ethylene oxide) group is —(CH$_2$CH$_2$O)$_n$NMe$_3$X, where n=2–100-); wherein X is selected from Br$^-$, I$^{31}$, B$_4^-$, CF$_3$SO$_3^-$, ammonium hexafluorophosphate, and tetrakis[3,5-bis(trifluoromethyl) phenyl]borate.

12. A method of imaging the nucleus in a cell, comprising the steps of:

exposing the cell to a polyhedral oligomeric silsesquioxane compound comprising a polycyclic compound consisting of a silicon/oxygen cage surrounded by tunable organic substitution groups attached to silicon atoms of the silicon/oxygen cage;

(i) wherein the tunable organic substitution groups are independently selected from the following structural formulae:

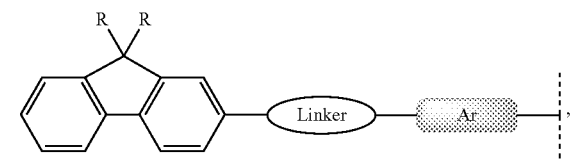

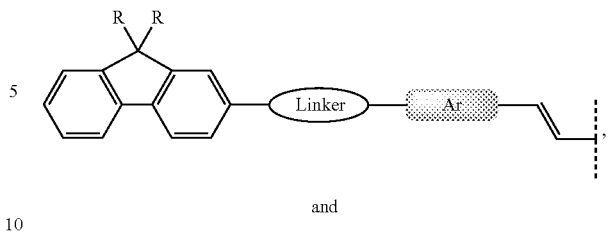

and

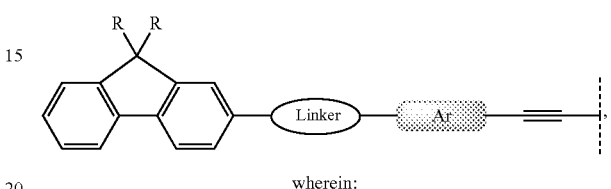

wherein:

Ar is an optionally substituted aromatic group;

Linker is a single bond, double bond, triple bond, or —CR$^1_m$; wherein R$^1$ is hydrogen, a halogen, a hydroxy group, an amino group, a C$_1$-C$_6$ alkyl group, a C$_2$-C$_6$alkenylgroup, a alkynyl group, or a C$_1$-C$_6$ alkoxy group; wherein the alkyl, alkenyl, alkynyl, or alkoxy groups may be optionally substituted with a halogen, a hydroxy group, a C$_1$-C$_4$ alkoxy group, or an amino group; and each R is independently hydrogen, a cationic alkyl side group, a cationic oligo(ethylene oxide) group, or a cationic poly(ethylene oxide) group, provided that at least one R is not hydrogen; or (ii) wherein the tunable organic substitution groups are independently selected from the following structural formulae:

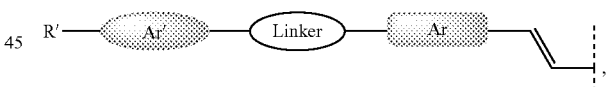

and

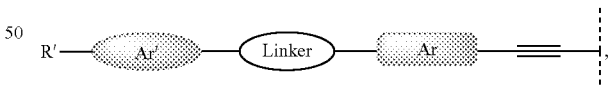

wherein:

each

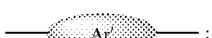

is independently selected from:

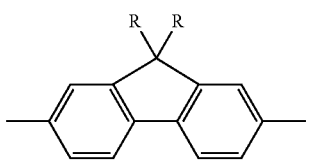

-continued

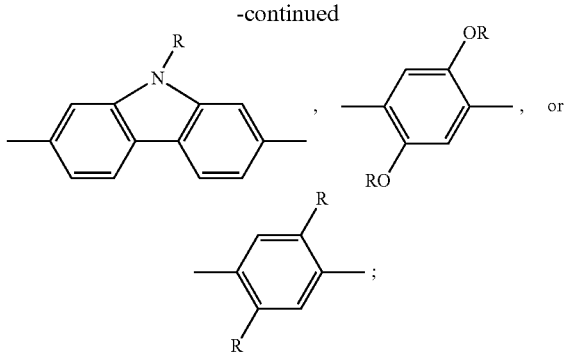

each Ar is independently an optionally substituted aromatic group;
each R is independently a cationic or anionic alkyl group, or a cationic or anionic oligo(ethylene oxide) group, or a cationic or anionic poly(ethylene oxide) group;
each Linker is a single bond, double bond, triple bond, —$CH_2$—, or —$CH_2CH_2$—; and
each R' is independently H or a terminal reactive group;
allowing the polyhedral oligomeric silsesquioxane compound to bind to the nucleus; and
assaying the cell to determine the location of the polyhedral oligomeric silsequioxane Compound within or on the cell.

13. The method of claim 12, wherein the polyhedral oligomeric silsesquioxane compound is represented by the following structural formula:

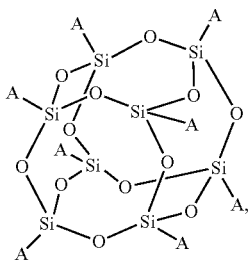

or an acceptable salt thereof, wherein:
each A is one of the tunable organic substitution groups and is independently selected from the following structural formulae:

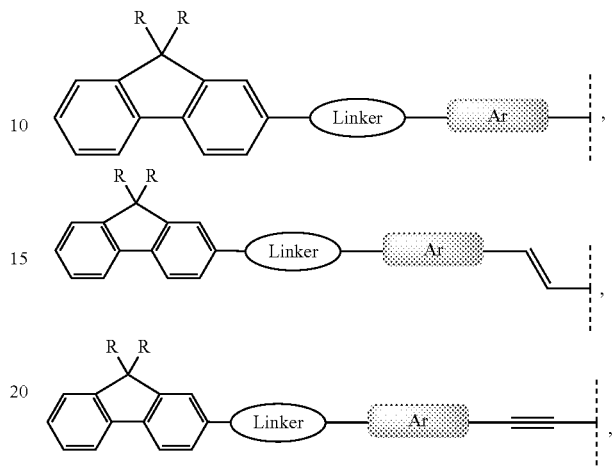

Ar is an optionally substituted aromatic group;
Linker is a single bond, double bond, triple bond, or —$CR^1_m$—; wherein $R^1$ is hydrogen, a halogen, a hydroxy group, an amino group, a $C_1$-$C_6$ alkyl group, a $C_2$-$C_6$ alkenyl group, a $C_2$-$C_6$ alkynyl group, or a $C_1$-$C_6$ alkoxy group; wherein the alkyl, alkenyl, alkynyl, or alkoxy groups may be optionally substituted with a halogen, a hydroxy group, a $C_1$-$C_4$ alkoxy group, or an amino group; and
each R is independently hydrogen, a cationic alkyl side group, a cationic oligo(ethylene oxide) group, or a cationic poly(ethylene oxide) group, provided that at least one R is not hydrogen.

14. The method of claim 12, where the polyhedral oligomeric silsesquioxane compound is

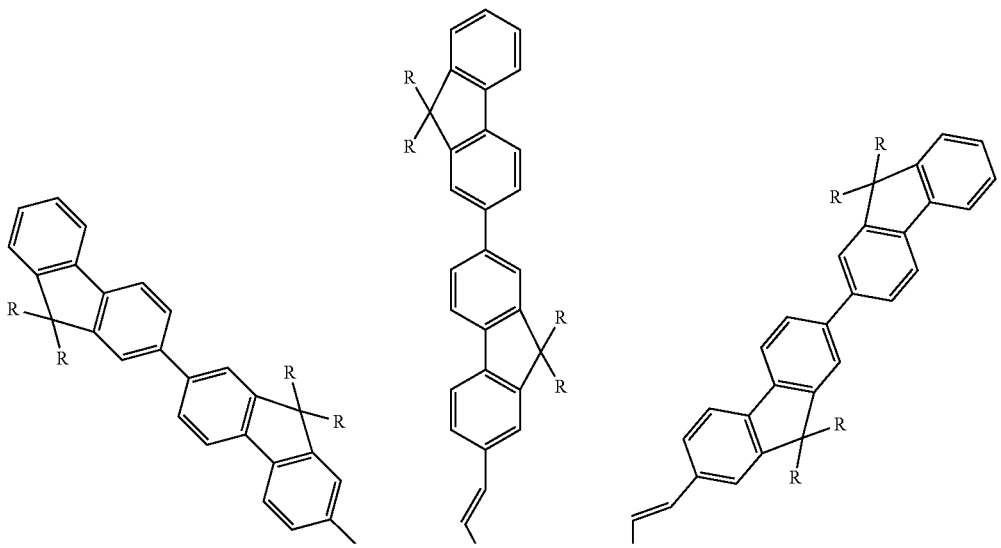

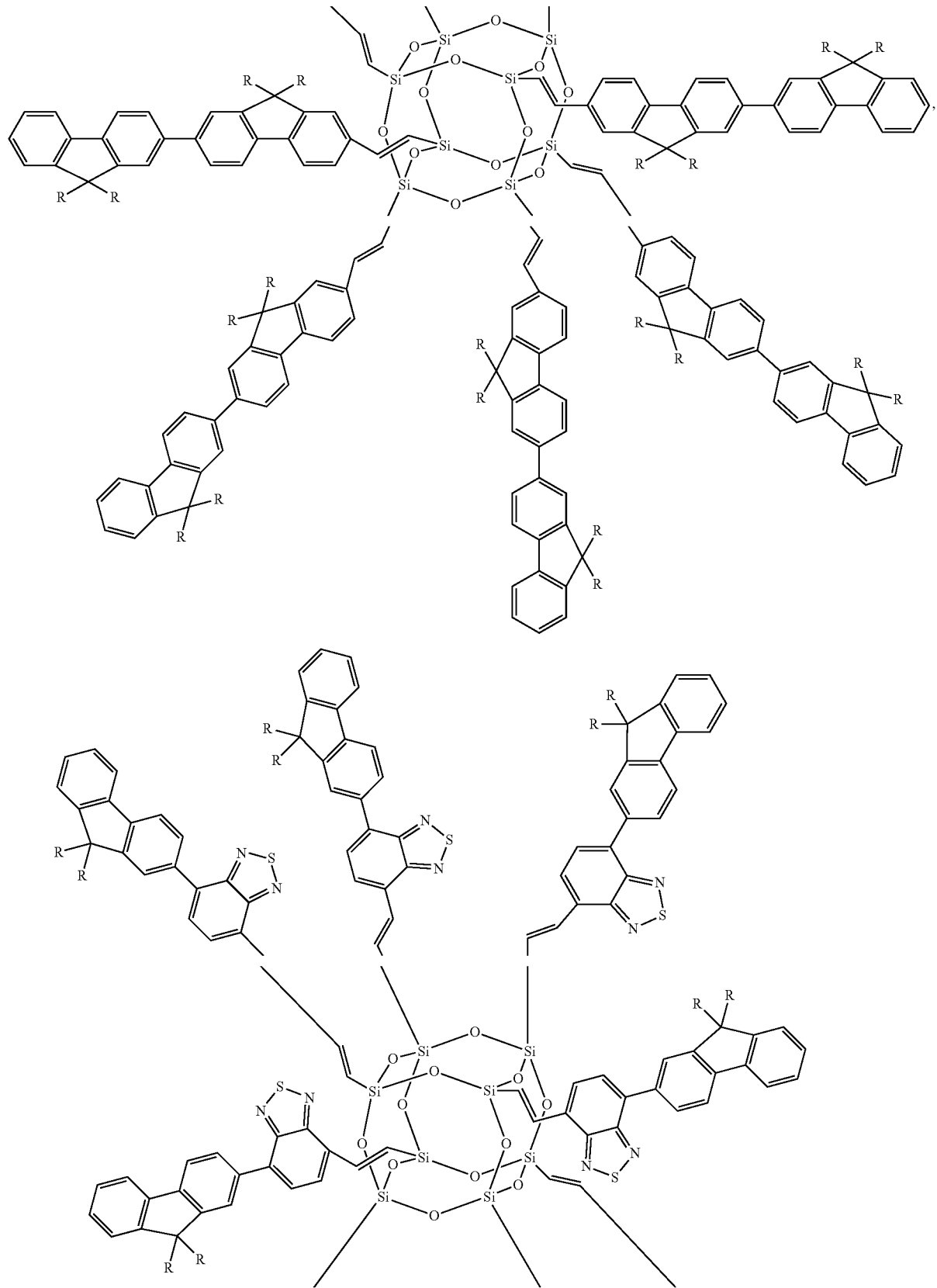

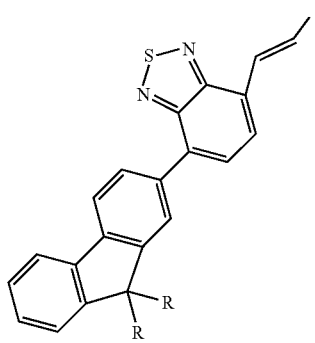

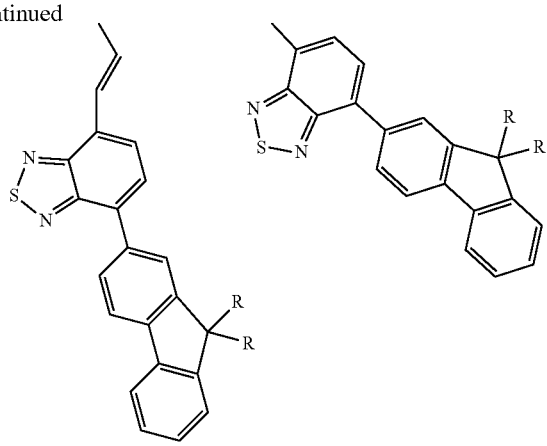

wherein R represents —(CH$_2$)$_6$N+(CH$_3$)$_3$Br$^-$.

15. The method of claim 12, wherein the polyhedral oligomeric silsesquioxane compound is represented by the following structural formula:

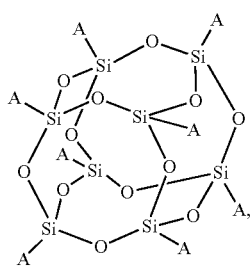

or an acceptable salt thereof, wherein:

each A is one of the tunable organic substitution groups and is independently selected from the following structural formulae:

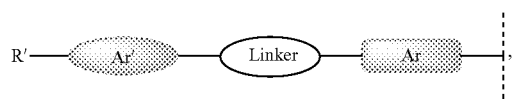

and

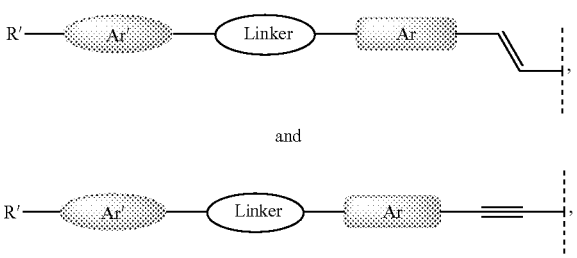

wherein:

each

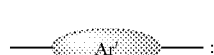

is independently selected from:

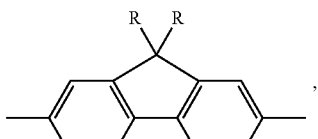

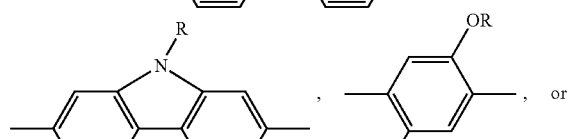

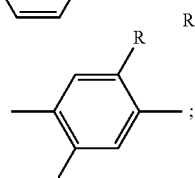

each Ar is independently an optionally substituted aromatic group;
each R is independently a cationic or anionic alkyl group, or a cationic or anionic oligo(ethylene oxide) group, or a cationic or anionic poly(ethylene oxide) group;
each Linker is a single bond, double bond, triple bond, —CH$_2$—, or —CH$_2$CH$_2$—; and
each R' is independently H or a terminal reactive group.

16. A method of quantifying a biomolecule, comprising the steps of:
exposing the biomolecule to a polyhedral oligomeric silsesquioxane compound comprising a polycyclic compound consisting of a silicon/oxygen cage surrounded by tunable organic substitution groups, attached to silicon atoms of the silicon/oxygen cage;
(i) wherein the tunable organic substitution groups are independently selected from the following structural formulae:

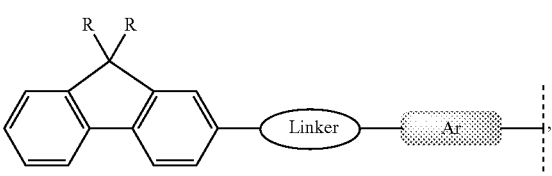

-continued

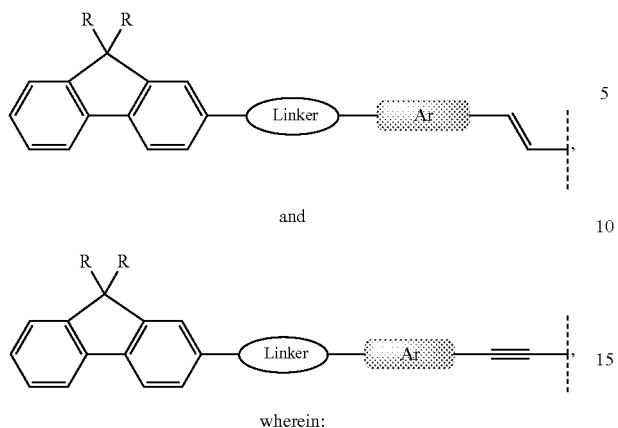

and wherein:

Ar is an optionally substituted aromatic group;
Linker is a single bond, double bond, triple bond, or —CR$^1_m$—; wherein R$^1$ is hydrogen, a halogen, a hydroxy group, an amino group, a $C_1$-$C_6$ alkyl group, a $C_2$-$C_6$ alkenyl group, a $C_2$-$C_6$ alkynyl group, or a $C_1$-$C_6$ alkoxy group; wherein the alkyl, alkenyl, alkynyl, or alkoxy groups may be optionally substituted with a halogen, a hydroxy group, a $C_1$-$C_4$ alkoxy group, or an amino group; and
each R is independently hydrogen, a cationic alkyl side group, a cationic oligo(ethylene oxide) group, or a cationic poly(ethylene oxide) group, provided that at least one R is not hydrogen; or
(ii) wherein the tunable organic substitution groups are independently selected from the following structural formulae:

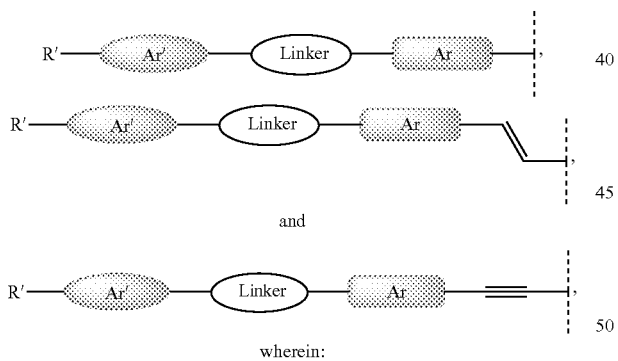

and wherein:

each

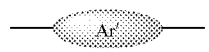

is independently selected from:

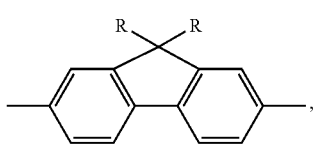

-continued

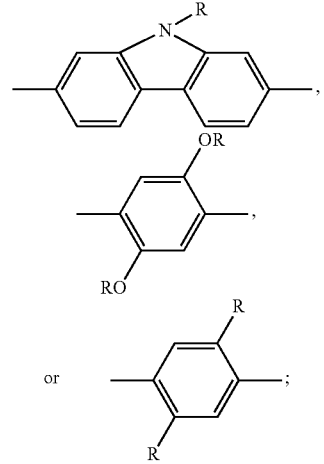

or each Ar is independently an optionally substituted aromatic group;
each R is independently a cationic or anionic alkyl group, or a cationic or anionic oligo(ethylene oxide) group, or a cationic or anionic poly(ethylene oxide) group;
each Linker is a single bond, double bond, triple bond, —CH$_2$—, or —CH$_2$CH$_2$—; and
each R' is independently H or a terminal reactive group;
allowing the polyhedral oligomeric silsesquioxane compound to bind to the biomolecule;
and assaying the polyhedral oligomeric silsesquioxane compound, thereby quantifying the biomolecule.

17. The method of claim 16, wherein the biomolecule is immobilized on a nanoparticle.

18. A method to detect a biological molecule in a test solution, comprising the steps of:
providing an aptamer capable of binding the biological molecule;
immobilizing the aptamer on a solid support;
incubating the immobilized aptamer with the test solution;
exposing the test solution to a polyhedral oligomeric silsesquioxane compound comprising a polycyclic compound consisting of a silicon/oxygen cage surrounded by tunable organic substitution groups, attached to silicon atoms of the silicon/oxygen cage;
(i) wherein the tunable organic substitution groups are independently selected from the following structural formulae:

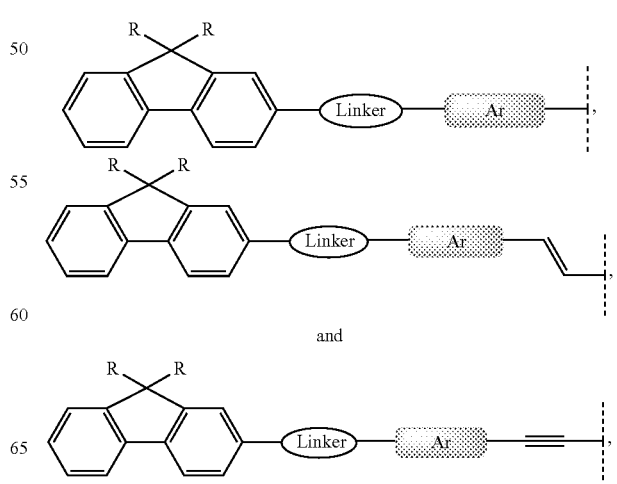

and

-continued wherein:

Ar is an optionally substituted aromatic group;
each Linker is a single bond, double bond, triple bond, —CH$_2$—or —CH$_2$CH$_2$—; and
each R is independently hydrogen, a cationic alkyl side group, a cationic oligo(ethylene oxide) group, or a cationic poly(ethylene oxide) group, provided that at least one R is not hydrogen; or
(ii) wherein the tunable organic substitution groups are independently selected from the following structural formulae:

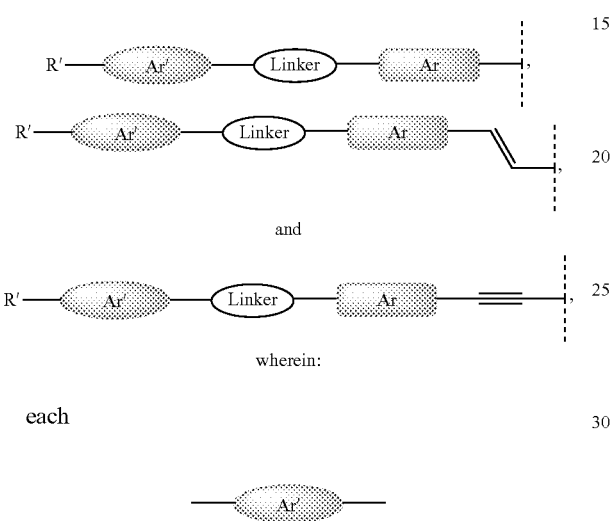

and wherein:

each

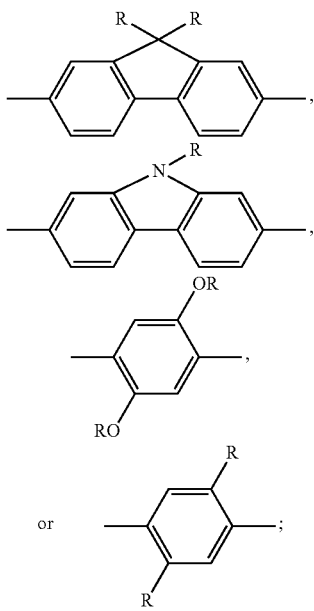

is independently selected from:

each Ar is independently an optionally substituted aromatic group;
each R is independently a cationic or anionic alkyl group, or a cationic or anionic oligo(ethylene oxide) group, or a cationic or anionic poly(ethylene oxide) group;
each Linker is a single bond, double bond, triple bond, —CH$_2$—or —CH$_2$CH$_2$—; and
each R' is independently H or a terminal reactive group;
and measuring the fluorescence of the test solution, thereby detecting the biological molecule.

19. The method of claim 18, wherein the polyhedral oligomeric silsesquioxane compound is represented by the following structural formula:

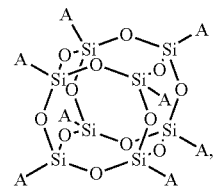

or an acceptable salt thereof, wherein:
each A is one of the tunable organic substitution groups and is independently selected from the following structural formulae:

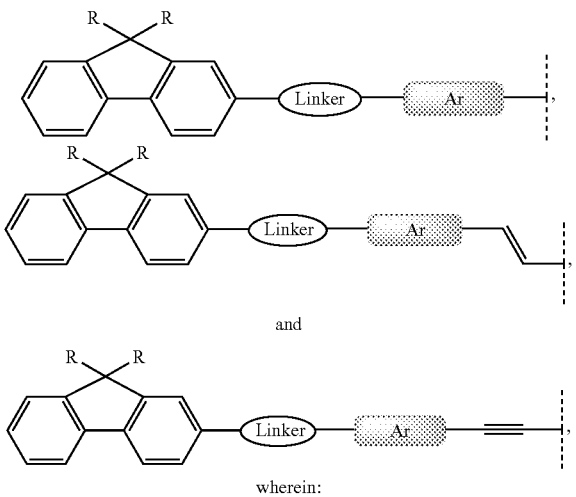

wherein:

Ar is an optionally substituted aromatic group;
each Linker is a single bond, double bond, triple bond, —CH$_2$—, or —CH$_2$CH$_2$—; and
each R is independently hydrogen, a cationic alkyl side group, a cationic oligo(ethylene oxide) group, or a cationic poly(ethylene oxide) group, provided that at least one R is not hydrogen.

20. The method of claim 18, wherein the polyhedral oligomeric silsesquioxane compound is represented by the following structural formula:

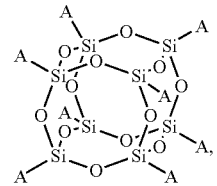

or an acceptable salt thereof, wherein:
each A is one of the tunable organic substitution groups and is independently selected from the following structural formulae:

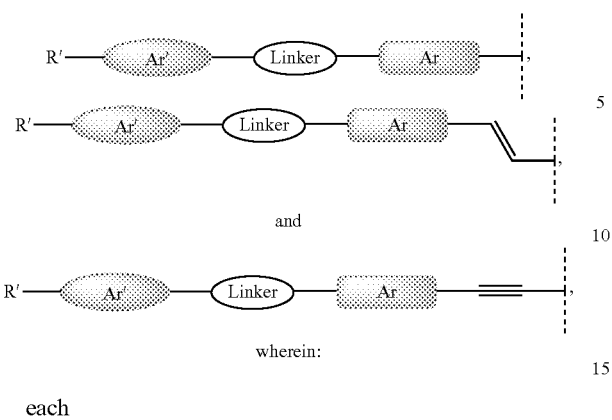

wherein:

each 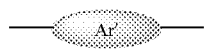 is independently selected from:

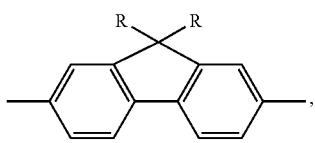

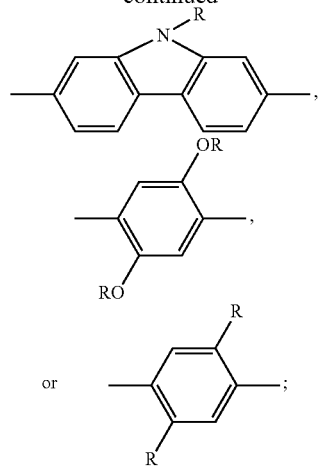

or 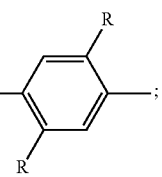 ;

each Ar is independently an optionally substituted aromatic group;

each R is independently a cationic or anionic alkyl group, or a cationic or anionic oligo(ethylene oxide) group, or a cationic or anionic poly(ethylene oxide) group;

each Linker is a single bond, double bond, triple bond, —CH$_2$—, or —CH$_2$CH$_2$—; and each R' is independently H or a terminal reactive group.

* * * * *